(12) United States Patent
Mogi

(10) Patent No.: US 12,270,018 B2
(45) Date of Patent: Apr. 8, 2025

(54) CULTURE ADDITIVE DIFFUSION MECHANISM, CULTURE CONTAINER, CULTURE SYSTEM, AND METHOD OF PRODUCING CELLS

(71) Applicant: YOKOGAWA ELECTRIC CORPORATION, Tokyo (JP)

(72) Inventor: Takeyuki Mogi, Musashino (JP)

(73) Assignee: Yokogawa Electric Corporation, Tokyo (JP)

(*) Notice: Subject to any disclaimer, the term of this patent is extended or adjusted under 35 U.S.C. 154(b) by 1293 days.

(21) Appl. No.: 16/963,762

(22) PCT Filed: Jan. 18, 2019

(86) PCT No.: PCT/JP2019/001558
§ 371 (c)(1),
(2) Date: Jul. 21, 2020

(87) PCT Pub. No.: WO2019/146531
PCT Pub. Date: Aug. 1, 2019

(65) Prior Publication Data
US 2021/0040431 A1    Feb. 11, 2021

(30) Foreign Application Priority Data

Jan. 24, 2018  (JP) .................... 2018-009460
Dec. 7, 2018  (JP) .................... 2018-230328

(51) Int. Cl.
C12M 1/00     (2006.01)
C12M 1/26     (2006.01)
(Continued)

(52) U.S. Cl.
CPC ............ *C12M 29/06* (2013.01); *C12M 33/14* (2013.01); *C12M 41/48* (2013.01); *C12N 5/0605* (2013.01);
(Continued)

(58) Field of Classification Search
CPC ...... C12M 29/06; C12M 33/14; C12M 41/48; C12M 29/04; C12M 35/08; C12M 41/32;
(Continued)

(56) References Cited

U.S. PATENT DOCUMENTS 5,998,588 A   12/1999  Hoffman et al.
6,486,213 B1  11/2002  Chen et al.
(Continued)

FOREIGN PATENT DOCUMENTS

CN        202187007        4/2012
EP        2944711 A1       11/2015
(Continued)

OTHER PUBLICATIONS

Mitsuhiro, E., et al., WO 2014/109379 A1, published Jul. 17, 2014, original and machine translation. (Year: 2014).*
(Continued)

*Primary Examiner* — Lydia Edwards
(74) *Attorney, Agent, or Firm* — RANKIN, HILL & CLARK LLP

(57) ABSTRACT

A culture additive diffusion mechanism (23) includes an additive retention unit (20) configured to retain an additive (21) used in a culture and a diffusion adjustment unit (22) configured to adjust a diffusion rate of the additive (21) from the inside of the additive retention unit (20) to the outside of the additive retention unit (20).

12 Claims, 28 Drawing Sheets

(51) Int. Cl.
*C12M 1/36* (2006.01)
*C12N 5/073* (2010.01)
*C12N 5/071* (2010.01)

(52) U.S. Cl.
CPC ........ *C12N 5/069* (2013.01); *C12N 2501/165* (2013.01)

(58) Field of Classification Search
CPC ...... B01L 2400/0672; C12N 2501/165; C12N 5/0605; C12N 5/069
See application file for complete search history.

(56) References Cited

U.S. PATENT DOCUMENTS

| 8,241,269 | B2 | 8/2012 | Massengale et al. |
| 2002/0055166 | A1* | 5/2002 | Cannon ................. C12M 41/00 435/303.1 |
| 2002/0169235 | A1 | 11/2002 | West et al. |
| 2005/0260743 | A1 | 11/2005 | Drake et al. |
| 2006/0115861 | A1 | 6/2006 | Shiotsuka et al. |
| 2009/0191270 | A1 | 7/2009 | Shiotsuka et al. |
| 2010/0055769 | A1 | 3/2010 | Kurt et al. |
| 2012/0040453 | A1 | 2/2012 | Zal |
| 2012/0156781 | A1 | 6/2012 | Takahashi et al. |
| 2014/0031750 | A1* | 1/2014 | Ordeig .............. A61M 5/14276 604/131 |
| 2015/0352209 | A1 | 12/2015 | Ebara et al. |
| 2018/0355296 | A1 | 12/2018 | Nakayama et al. |
| 2019/0040359 | A1 | 2/2019 | Nakayama et al. |

FOREIGN PATENT DOCUMENTS

| JP | 2013031408 | 2/2013 |
| JP | 2014-113109 A | 6/2014 |
| JP | 5594658 B2 | 9/2014 |
| JP | 5881031 B2 | 3/2016 |
| JP | 6111510 B1 | 4/2017 |
| WO | 2014/109379 A1 | 7/2014 |
| WO | 2014/161036 A1 | 10/2014 |

OTHER PUBLICATIONS

Lotz et al., "Sustained Levels of FGF2 Maintain Undifferentiated Stem Cell Cultures with Biweekly Feeding", PLOS ONE, Feb. 2013, vol. 8, Issue 2, e56289, pp. 1-10.

Sanromán-Iglesias et al., "Conjugated Polymers As Molecular Gates for Light-Controlled Release of Gold Nanoparticles", ACS Applied Materials &Interfaces, Jul. 2015, vol. 7, pp. 15692-15695.

Hribar et al., "Enhanced Release of Small Molecules from Near-Infrared Light Responsive Polymer-Nanorod Composites", ACS NANO, 2011, vol. 5, No. 4, pp. 2948-2956; for European Patent Application No. 19743730.4.

D'Anour et al., "Production of pancreatic hormone-expressing endocrine cells from human embryonic stem cells", Nature Biotechnology, 2006, vol. 24, No. 11, pp. 1392-1401, total 11 pages.

"Building the Future of Science and Society Together", Science Agora, IPS Trend, Dec. 2014 and its partial English translation.

Isozaki et al., "Ultrasound-Induced Gelation of Organic Fluids with Metallated Peptides", Angewandte Chemie, 2007, pp. S1-S32, total 33 pages.

Conrad et al., "Tunable, Temperature-Responsive Polynorbornenes with Side Chains Based on an Elastin Peptide Sequence", NIH Public Access, Author Manuscript, Angew Chem Int Ed Engl. 2009, 48(44), total 10 pages.

Golnar Dorraj et al., "Preparation and Characterization of Thermoresponsive In-situ Forming Poloxamer Hydrogel for Controlled Release of Nile red-loaded Solid Lipid Nanoparticles", Journal of Pharmaceutical Sciences, 2013, vol. 9, No. 4, pp. 39-50.

Haifei Zhang et al., "Thermoresponsive "Particle Pumps": Activated Release of Organic Nanoparticles from Open-Cell Macroporous Polymers", Advanced Materials, 2007, vol. 19, pp. 2439-2444.

Khulan Sergelen et al., "Free-standing hydrogel-particle composite membrane with dynamically controlled permeability", Biointer phases, Dec. 6, 2017, vol. 12, No. 5, 051002(pp. 1-9).

* cited by examiner

FIG. 2
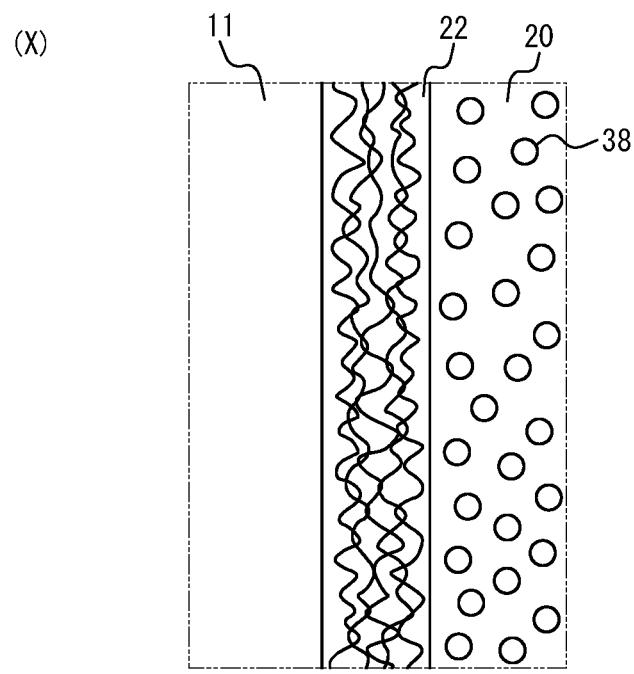
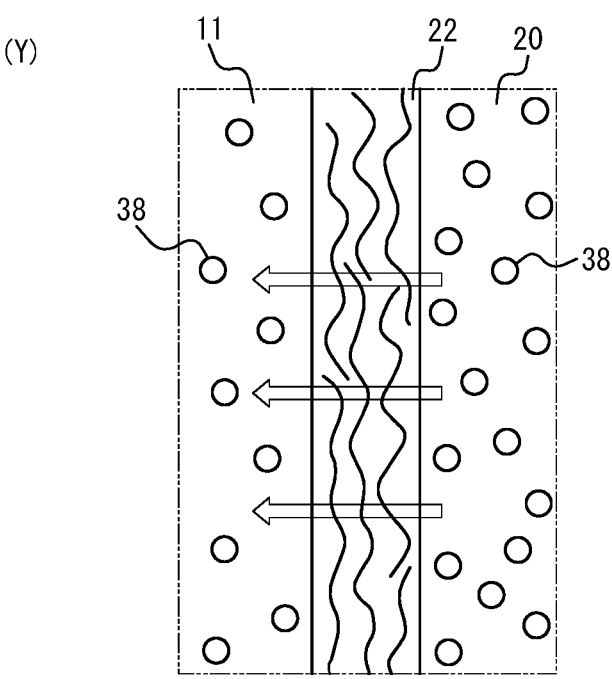

FIG. 3
(X)
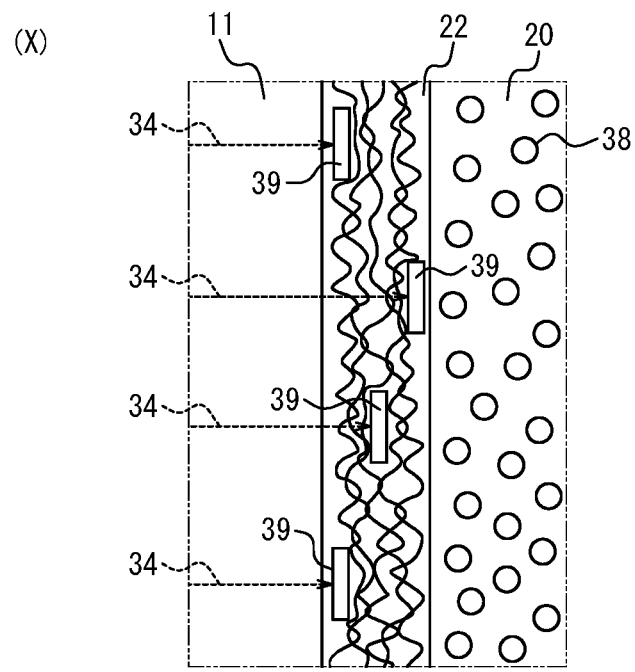
(Y)
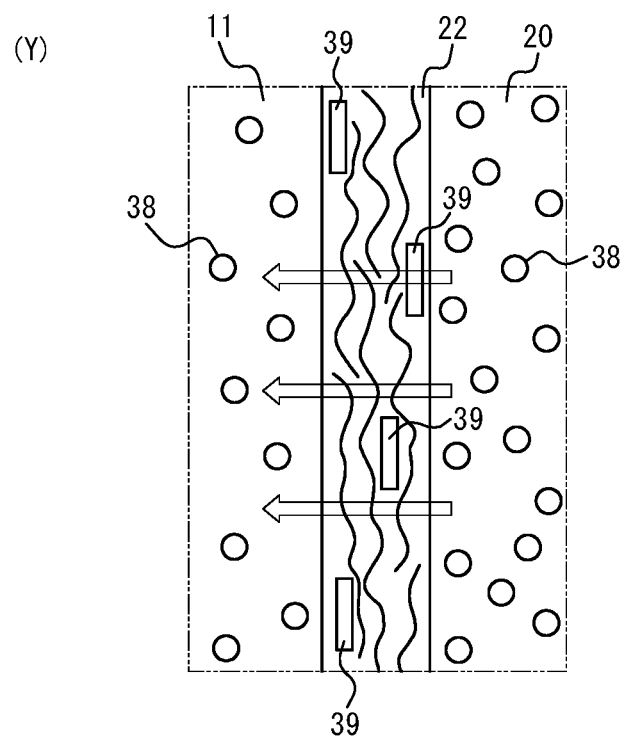

FIG. 19
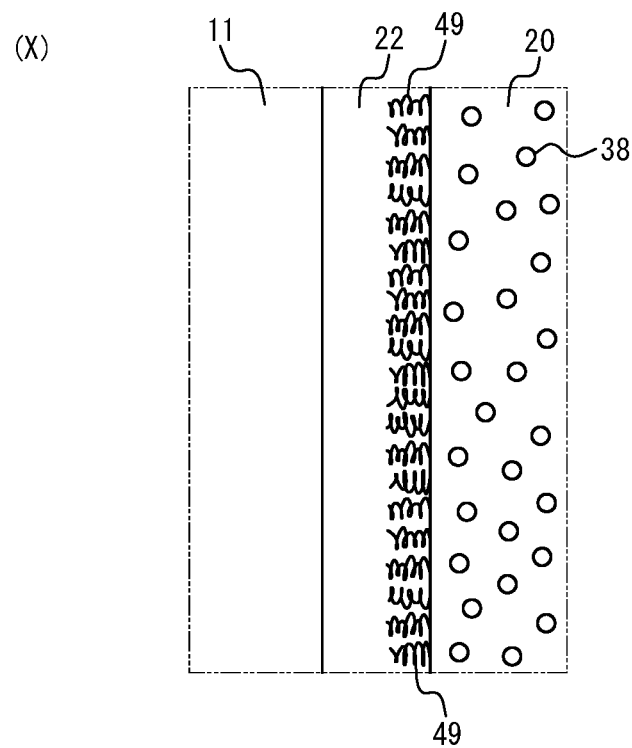
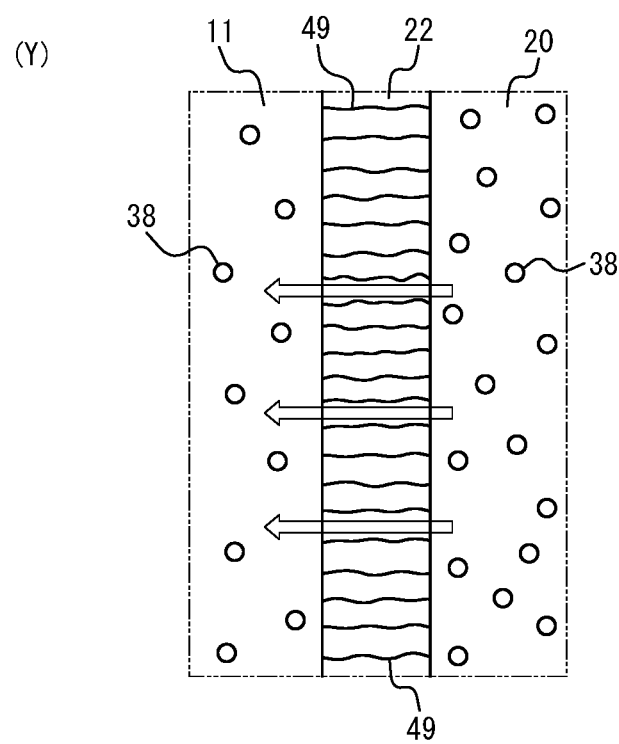

FIG. 20
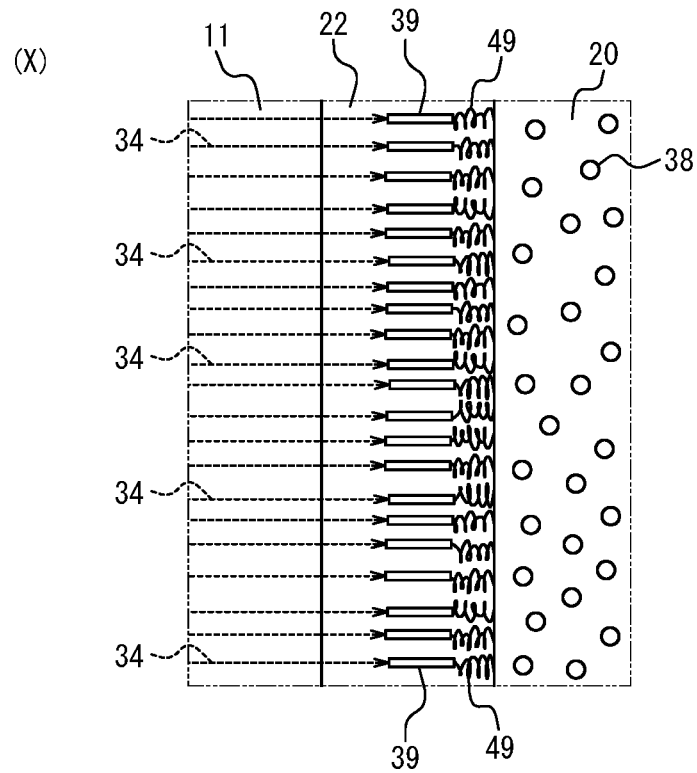
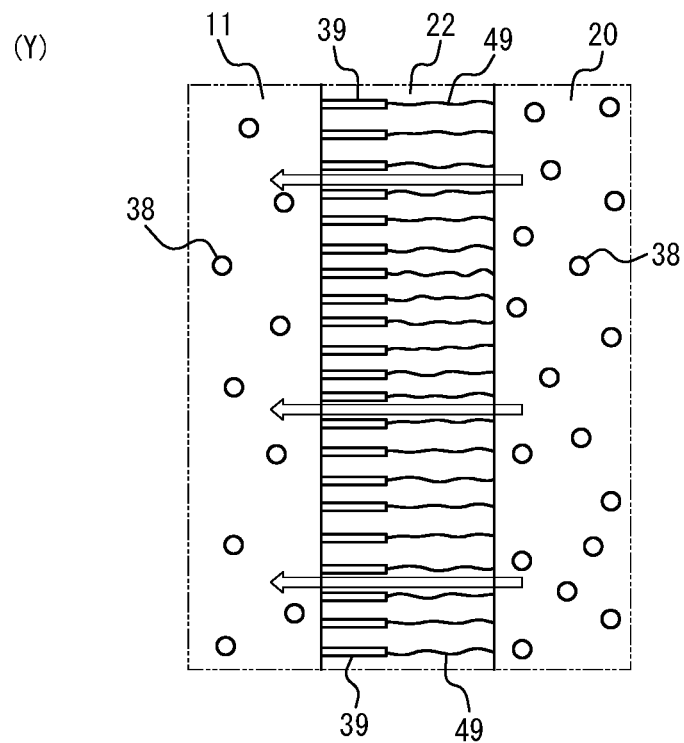

Less ◁▬▬▬▬▶ More

FIG. 27
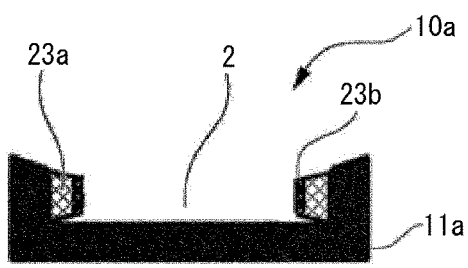
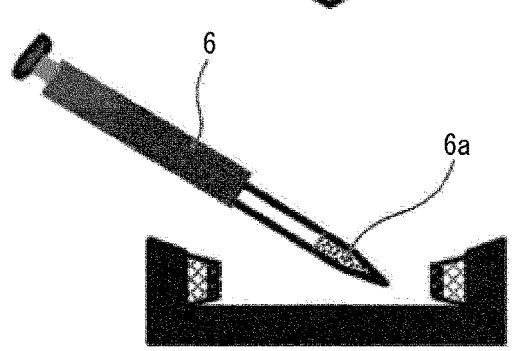
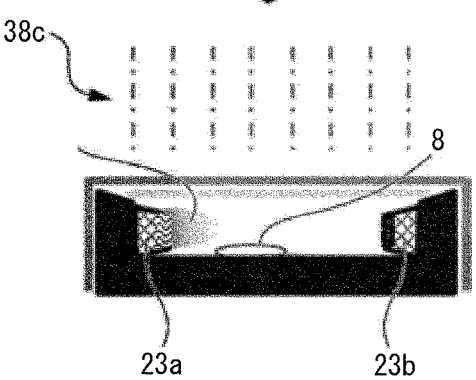
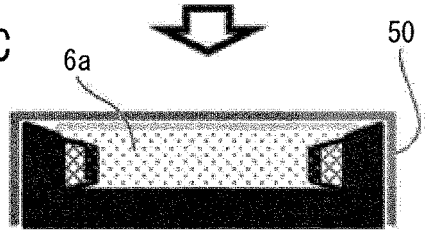
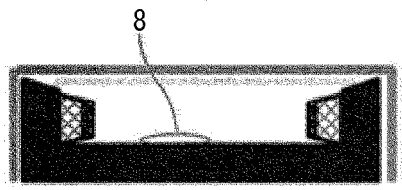
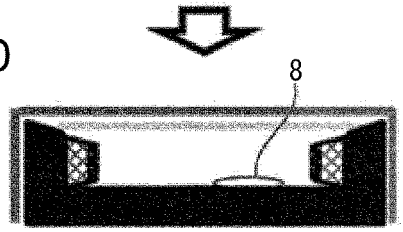

CULTURE ADDITIVE DIFFUSION MECHANISM, CULTURE CONTAINER, CULTURE SYSTEM, AND METHOD OF PRODUCING CELLS

CROSS-REFERENCE TO RELATED APPLICATION

The present application claims priority to and the benefit of Japanese Patent Application No. 2018-009460 filed Jan. 24, 2018, and Japanese Patent Application No. 2018-230328 filed Dec. 7, 2018, the entire contents of which are incorporated herein by reference.

TECHNICAL FIELD

The present disclosure relates to a culture additive diffusion mechanism, a culture container, a culture system, and a method of producing cells.

BACKGROUND

With advances in regenerative medicine in recent years, demand has increased for techniques to culture cells efficiently. Various additives need to be added to the culture medium at appropriate times and in appropriate amounts to culture cells efficiently and achieve well-formed tissue. Attempts are thus being made to develop techniques for adding additives efficiently during culturing.

Non-patent literature (NPL) 1 discloses a method for adding an additive to a culture medium manually. NPL 2 discloses a method for adding an additive to a culture medium automatically using a dispenser. Patent literature (PTL) 1 discloses a culture medium exchange system that includes a supply-side liquid transfer pump for sending culture medium to a cell culture container and a discharge-side liquid transfer pump for sending a culture fluid from the cell culture container to a drainage container. PTL 2 discloses a growth inducement system for supplying a culture fluid that includes cytokines, secreted by a secreting body, to a growth inducement target. PTL 3 discloses a method for introducing liquids with different compositions from a plurality of through holes to produce a concentration gradient of a substance inside a micro space for culturing cells.

CITATION LIST

Patent Literature

PTL 1: JP2014-113109A
PTL 2: JP6111510B2
PTL 3: JP5594658B2

Non-Patent Literature

NPL 1: Kevin A D'Amour et al., "Production of pancreatic hormone-expressing endocrine cells from human embryonic stem cells.", Nature Biotechnology, Oct. 19, 2006, volume 24 number 11, 1392-1401.
NPL 2: "Science Agora: Building the Future of Science and Society Together" [online], Japan Science and Technology Agency Home Page, accessed Nov. 2, 2018.

SUMMARY

Technical Problem

With the methods disclosed in NPL 1 and 2, however, loss occurs due to additive being adsorbed on the tip. Moreover, contamination may occur. To add an additive using the techniques disclosed in PTL 1 and 2, a flow path for liquid transfer of culture medium with the additive added therein needs to be provided. These techniques thus have the disadvantage of a complex apparatus configuration. The micro fluid dispenser used in the method disclosed in PTL 3 has a high production cost and requires numerous minute flow paths, which entails the risk of fluid leakage.

The present disclosure aims to provide a technique enabling efficient and simple control of the addition of an additive to a culture medium by adding the additive using the phenomenon of diffusion.

Solution to Problem

A culture additive diffusion mechanism according to an embodiment includes an additive retention unit configured to retain an additive used in a culture and a diffusion adjustment unit configured to adjust a diffusion rate of the additive from the inside of the additive retention unit to the outside of the additive retention unit. Providing the diffusion adjustment unit and adding the additive using the phenomenon of diffusion enables efficient and simple control of addition of the additive to a culture medium.

In an embodiment, the diffusion adjustment unit of the culture additive diffusion mechanism may change the diffusion rate of the additive in accordance with a change in at least one environmental parameter. Changing the diffusion rate of the additive using an environmental parameter in this way enables control of the addition of the additive with a simple configuration, without the use of a complicated apparatus configuration.

In the culture additive diffusion mechanism according to an embodiment, the diffusion adjustment unit may include a stimulus-responsive material and may be configured to change the diffusion rate of the additive in accordance with at least one stimulus. Changing the diffusion rate of the additive using a stimulus-responsive material in this way enables control of the addition of the additive with a simple configuration, without the use of a complicated apparatus configuration.

In the culture additive diffusion mechanism according to an embodiment, the diffusion adjustment unit may further include a near-infrared absorber that absorbs near-infrared rays, the stimulus-responsive material may be a temperature-responsive material, and the temperature-responsive material may change the diffusion rate of the additive in accordance with a temperature change of the near-infrared absorber. Such use of a near-infrared absorber that absorbs near-infrared rays and a temperature-responsive material that changes the diffusion rate of the additive in accordance with a temperature change of the near-infrared absorber enables adjustment of the diffusion rate of the additive by use of local heating, through irradiation of near-infrared rays, of the near-infrared absorber and the temperature-responsive material located close to the near-infrared absorber. This enables control of the addition of the additive to the culture target, such as cultured cells, in a less invasive manner.

In an embodiment, a culture container includes a culture additive diffusion mechanism of the present disclosure and a culture unit into which a culture target and a culture medium are introduced. The culture unit and the culture additive diffusion mechanism are connected via the diffusion adjustment unit. Such a culture container enables culturing of a culture target, such as cells, while efficiently and easily adjusting addition of the additive to the culture medium using the phenomenon of diffusion of the additive via the diffusion adjustment unit.

In an embodiment, the culture container may include a plurality of the culture units. When the culture container includes a plurality of the culture units in this way, cells can be cultured simultaneously in the plurality of culture units. The culture target, such as cells, can thereby be mass-produced efficiently.

In an embodiment, the culture container may include a plurality of the culture additive diffusion mechanisms. When the culture container includes a plurality of the culture additive diffusion mechanisms in this way, the amount and timing of the additive that is added can be adjusted more freely.

In the culture container of an embodiment, the culture additive diffusion mechanisms may retain different types of the additive from each other. As a result of the culture additive diffusion mechanisms retaining different types of additives from each other, culturing can be carried out while adjusting the addition of a plurality of types of additives. This is helpful for culturing that requires a plurality of types of additives.

A culture system in an embodiment includes a culture container according to an embodiment and a culture management apparatus. The culture management apparatus includes an acquisition interface, a controller, and a transmitter. The acquisition interface is configured to acquire a culture protocol that defines at least an addition procedure of the additive. The controller is configured to refer to the culture protocol to generate transmitter control information. The transmitter is configured to transmit a control signal for adjusting the diffusion rate of the additive to the diffusion adjustment unit based on the transmitter control information. The diffusion adjustment unit is configured to adjust the diffusion rate of the additive based on the control signal. This culture system enables culturing of a culture target, such as cells, while efficiently and simply controlling addition of the additive to the culture medium.

In the culture system of an embodiment, the culture protocol may define at least one piece of information selected from among the group consisting of an addition amount of the additive, an addition duration, and a timing. When the culture protocol thus defines at least one piece of information selected from among the group consisting of an addition amount of the additive, an addition duration, and a timing, the culture system can acquire the culture protocol and adjust at least one selected from among the group consisting of the addition amount of the additive, the addition duration, and the timing.

In the culture system according to an embodiment, a signal transmission path for transmitting the control signal to the diffusion adjustment unit may be connected to the transmitter. When a signal transmission path for transmitting the control signal to the diffusion adjustment unit is connected to the transmitter in this way, the control signal can be transmitted accurately to the diffusion adjustment unit.

In an embodiment, the culture system may further include a plurality of the culture containers and a transport unit configured to move at least one culture container among the plurality of culture containers to a predetermined position. The controller may be configured to refer to the culture protocol to generate, for each culture container among the plurality of culture containers, transmitter control information for adding the additive to the culture container. Based on the transmitter control information corresponding to the culture container located at the position, the transmitter may be configured to transmit the control signal to the diffusion adjustment unit of the culture container moved to the position. When transmitter control information is generated for each culture container and the control signal is transmitted to each culture container transported to a predetermined position in this way, the culture target, such as cells, can efficiently be mass-produced automatically.

In an embodiment, the culture system may further include a culture medium supply unit configured to supply culture medium to the culture unit. The culture medium supply unit may include a culture medium storage unit, a culture medium preservation unit, a culture medium transfer unit, and a culture medium transfer route. The culture protocol may define a supply procedure of the culture medium. The controller many be configured to refer to the culture protocol to generate culture medium supply unit control information. The culture medium supply unit may be configured to supply the culture medium to the culture unit based on the culture medium supply unit control information. When the culture medium supply unit supplies the culture medium to the culture unit based on the culture medium supply unit control information in this way, the supply of the culture medium can also be automated. This enables the culture target, such as cells, to be cultured more efficiently.

In an embodiment, the culture system may further include a culture medium supply unit configured to supply culture medium to the culture unit. The culture medium supply unit may include a culture medium storage unit, a culture medium preservation unit, a culture medium transfer unit, and a culture medium transfer route. At least a portion of the culture container may be a semi-permeable membrane unit formed by a semi-permeable membrane. A fluid connection may be formed between the culture container and the culture medium transfer route via the semi-permeable membrane unit. A component of the culture medium supplied from the culture medium supply unit via the semi-permeable membrane unit and the culture medium inside the culture container may be exchanged. When the components of the culture medium supplied from the culture medium supply unit and the culture medium in the culture container are exchanged via the semi-permeable membrane unit in this way, the risk of contamination can be reduced, and the culture medium can be used efficiently.

In an embodiment, the culture system may further include a culture target state measurement unit configured to measure a state of the culture target in the culture unit. The controller may be configured to refer additionally to a measurement result of the state of the culture target by the culture target state measurement unit to generate the transmitter control information. When the transmitter control information is generated with reference to the measurement result of the state of the culture target in this way, the additive can be added suitably in accordance with the state of the culture target, such as cells.

In an embodiment, the culture system may further include an additive measurement unit configured to measure a concentration of the additive included in the culture medium in the culture unit. The controller may be configured to refer additionally to a measurement result of the concentration of the additive by the additive measurement unit to generate the transmitter control information. When the transmitter control information is generated with reference to the measurement result of the concentration of the additive in this way, the additive can be added while the concentration of the additive is monitored. This enables a suitable amount of the additive to be added reliably.

In an embodiment, the culture system may include a culture environment maintenance unit for maintaining a physical parameter inside the culture unit within a certain range. When a physical parameter inside the culture unit is maintained within a certain range by the culture environment maintenance unit in this way, culturing can be carried out while maintaining a good culture environment.

A culture system in an embodiment may include a culture container and a culture management apparatus. The culture container may include a plurality of culture units into which a culture target and a culture medium are introduced and a plurality of culture additive diffusion mechanisms provided for the plurality of culture units. Each culture additive diffusion mechanism may include a diffusion adjustment unit and an additive retention unit. The culture management apparatus may include an acquisition interface, a controller, and a transmitter. The acquisition interface may be configured to acquire a culture protocol that defines at least an addition procedure of the additive. The controller may be configured to refer to the culture protocol to generate transmitter control information. The transmitter may be configured to transmit a control signal for adjusting the diffusion rate of the additive to the plurality of diffusion adjustment units based on the transmitter control information. The diffusion adjustment units may be configured to adjust the diffusion rate of the additive to the plurality of culture units based on the control signal. This culture system enables efficient and simple control of the addition of the additive to the culture medium of the plurality of culture units, thereby enabling efficient culturing of a large quantity of a culture target, such as cells.

A culture system in an embodiment includes a culture container and a culture management apparatus. The culture container includes a plurality of culture additive diffusion mechanisms and a culture unit into which a culture medium is introduced. Each culture additive diffusion mechanism includes a diffusion adjustment unit and an additive retention unit. The culture management apparatus includes an acquisition interface, a controller, and a transmitter. A plurality of signal transmission paths for transmitting a control signal to the diffusion adjustment units are connected to the transmitter. The acquisition interface is configured to acquire a culture protocol that defines at least an addition procedure of the additive. The controller is configured to refer to the culture protocol to generate transmitter control information. The transmitter is configured to transmit a control signal for adjusting the diffusion rate of the additive to the plurality of diffusion adjustment units via the plurality of signal transmission paths based on the transmitter control information. The diffusion adjustment units are configured to adjust the diffusion rate of the additive to the plurality of culture units based on the control signal. This culture system can transmit the control signal without crosstalk even when the plurality of diffusion adjustment units are located near each other. This enables more accurate control of diffusion of the additive.

In an embodiment, a method of producing cells uses the culture system according to an embodiment. Such a method of producing cells enables cell production while efficiently and easily adjusting the addition of additive to a culture medium.

In an embodiment, a method of producing cells may be a method of producing cells using a culture system that includes a culture container according to the present disclosure and a culture management apparatus. The culture management apparatus may include an acquisition interface, a controller, and a transmitter. The method may include acquiring, using the acquisition interface, a culture protocol that defines at least an addition procedure of the additive; referring, using the controller, to the culture protocol to generate transmitter control information; transmitting, using the transmitter, a control signal for adjusting the diffusion rate of the additive to the diffusion adjustment unit based on the transmitter control information; and adjusting, using the diffusion adjustment unit, the diffusion rate of the additive based on the control signal. Such a method of producing cells enables cell production while efficiently and easily adjusting the addition of additive to a culture medium.

[1] A culture additive diffusion mechanism according to an embodiment is a cell culture carrier for culturing cells. The cell culture carrier carries additive, which is an agent, on a cell culture stimulus-responsive substrate that includes a stimulus-responsive polymer and a control signal receiving material.

[2] In a cell culture carrier according to an embodiment, the additive may be enclosed in a porous material, and the cell culture stimulus-responsive substrate may be caused to carry the porous material and the additive.

[3] In a cell culture carrier according to an embodiment, the stimulus-responsive polymer material may be a temperature-responsive polymer material.

[4] In a cell culture carrier according to an embodiment, the control signal receiving material may be an organic compound, a metal structure, or a carbon material.

[5] In a cell culture carrier according to an embodiment, the metal structure may be gold nanorods.

[6] In a cell culture carrier according to an embodiment, the additive may be a protein such as an enzyme, a cytokine, a differentiation-inducing factor, or an antibody; a peptide such as a hormone; an antibiotic; a low molecular weight compound such as an amino acid, glucose, or retinoic acid; a nucleic acid such as DNA; nanoparticles; or liposomes.

[7] In a cell culture carrier according to an embodiment, the control signal received by the control signal receiving material may be near-infrared light.

[8] A culture container according to an embodiment may be a cell culture container for culturing cells and may include a cell culture carrier, in which additive is carried on a cell culture stimulus-responsive substrate including a stimulus-responsive polymer material and a control signal receiving material, and a cell culture unit that is a culture unit for culturing cells.

[9] In a cell culture container according to an embodiment, the additive may be enclosed in a porous material, and the cell culture stimulus-responsive substrate may be caused to carry the porous material and the additive.

[10] In a cell culture container according to an embodiment, the stimulus-responsive polymer material may be a temperature-responsive polymer material.

[11] In a cell culture container according to an embodiment, the control signal receiving material may be an organic compound, a metal structure, or a carbon material.

[12] In a cell culture container according to an embodiment, the metal structure may be gold nanorods.

[13] In a cell culture container according to an embodiment, the additive may be a protein such as an enzyme, a cytokine, a differentiation-inducing factor, or an antibody; a peptide such as a hormone; an antibiotic; a low molecular weight compound such as an amino acid, glucose, or retinoic acid; a nucleic acid such as DNA; nanoparticles; or liposomes.

[14] In a cell culture container according to an embodiment, the control signal received by the control signal receiving material may be near-infrared light.

[1] to [14] can provide a cell culture carrier or a cell culture container that is capable of detailed control of the supply of additive, enables culturing of a large quantity of cells, and can be produced at low cost.

Advantageous Effect

The present disclosure can provide a technique enabling efficient and simple control of the addition of an additive to a culture medium by adjusting the diffusion rate of the additive.

BRIEF DESCRIPTION OF THE DRAWINGS

In the accompanying drawings:

FIG. 1A illustrates the perimeter of an additive retention unit being surrounded by an impermeable unit and a diffusion adjustment unit, FIG. 1B illustrates the entire perimeter of the additive retention unit being surrounded by the diffusion adjustment unit, and FIG. 1C illustrates a stimulus-responsive material being caused to function as both the additive retention unit and the diffusion adjustment unit;

FIG. 2 illustrates the change in the diffusion rate of an additive via a membrane structure that includes a temperature-responsive material;

FIG. 3 illustrates how transmission of near-infrared rays to a membrane structure including a temperature-responsive material and a near-infrared absorber yields a change in the diffusion rate of an additive via the membrane structure;

FIG. 5A illustrates the plurality of culture units arranged to surround a culture additive diffusion mechanism, and FIG. 5B illustrates the plurality of culture units arranged on one surface of a culture additive diffusion mechanism;

FIG. 19 illustrates the change in the diffusion rate of an additive via a membrane structure that includes a temperature-responsive material;

FIG. 20 illustrates how transmission of near-infrared rays to a membrane structure including a temperature-responsive material and a near-infrared absorber yields a change in the diffusion rate of an additive via the membrane structure;

FIGS. 27A to 27G schematically illustrate a cell culture method that uses an example of a cell culture container;

DETAILED DESCRIPTION

Figure 1A:
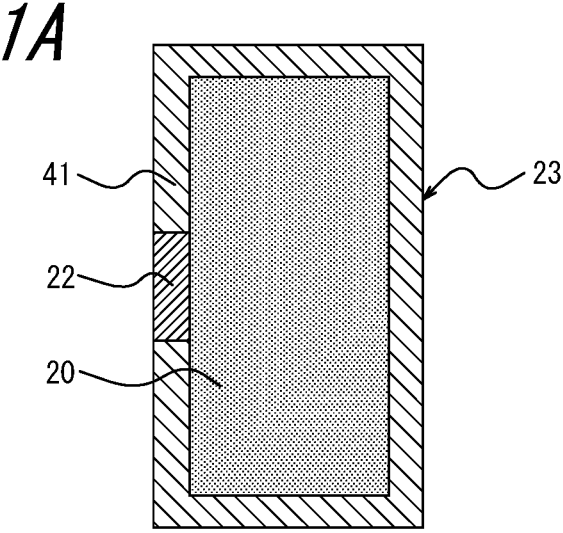
FIGS. 1A to 1C are cross-sections illustrating an example of a culture additive diffusion mechanism, where

Embodiments of the present disclosure are described below based on the drawings. Identical reference signs in the drawings indicate identical or similar constituent elements.

[Culture Additive Diffusion Mechanism]

A culture additive diffusion mechanism of the present disclosure can be used when adding additive to a culture medium for culturing a culture target, such as cells, and includes an additive retention unit configured to retain the additive used to culture the culture target and a diffusion adjustment unit configured to adjust a diffusion rate of the additive from the inside of the additive retention unit to the outside of the additive retention unit. Provision of the diffusion adjustment unit that adjusts the diffusion rate of the additive from the inside of the additive retention unit to the outside of the additive retention unit enables appropriate adjustment of the amount of additive that diffuses to the outside of the additive retention unit via the diffusion adjustment unit and appropriate adjustment of the timing of addition. Hence, providing the culture additive diffusion mechanism in a culture container as described below, for example, enables control of the addition of the additive to the culture medium.

As described above, the main method for adding additive to a culture medium has conventionally been to add the additive to a fluid and then use convection of the liquid to add the additive. By contrast, the culture additive diffusion mechanism of the present disclosure is not based on the movement of a fluid, but rather adds an additive using the phenomenon of diffusion of molecules. A flow path for causing a fluid to move therefore need not be provided, unlike a conventional technique. The culture additive diffusion mechanism of the present disclosure can thereby control the addition of an additive with a simpler apparatus configuration than with a conventional technique. Furthermore, there is no risk of the additive being adsorbed on the tip, unlike a method for adding an additive manually or with a dispenser. A method of adding an additive manually or with a dispenser also harbors the risk of contamination due to tainting of the tip. The culture additive diffusion mechanism of the present disclosure, however, enables control of the addition of an additive without removing the culture additive diffusion mechanism from the culture container or the like during culturing. The risk of contamination due to addition of an additive is thereby reduced. Accordingly, the culture additive diffusion mechanism of the present disclosure enables more efficient control of the addition of an additive than a method of adding an additive manually or with a dispenser.

Moreover, the culture additive diffusion mechanism of the present disclosure enables addition of an additive to cells in a form closer to the state in which substances are supplied to cells inside an organism. In other words, to supply a substance to cells in a multicell organism, the following systems are used in combination: (i) to supply a substance necessary for the whole body, a system to circulate a liquid including the substance throughout the body with a pump mechanism, such as the heart, is used, and (ii) to supply a substance necessary locally, a system to supply a minute amount of a substance secreted by a cell to another cell by diffusion is used. Conventionally, a technique such as the former system (i) has been used to add an additive to cells by convection of a fluid including the additive, but the application, to culturing, of a method for adding an additive using the phenomenon of diffusion as in the latter system (ii) has not been considered. Learning from the latter system (ii), I discovered that adding an additive using the phenomenon of diffusion enables additives, such as a differentiation-inducing factor and a cell growth factor, that are supplied by local diffusion in an organism to be added in a form closer to the state in which substances are supplied to cells inside an organism. This discovery led to the culture additive diffusion mechanism according to the present disclosure. The culture additive diffusion mechanism of the present disclosure enables addition of an additive to cells in a form closer to the state in which substances are supplied to cells inside an organism, thereby enabling culturing that more faithfully replicates the environment in an organism.

Figure 1B:
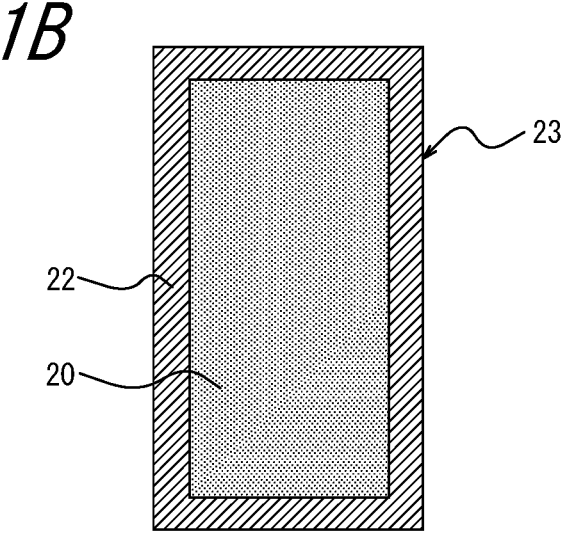

An example of a specific form of the culture additive diffusion mechanism is described with reference to FIGS. 1A and 1B, which schematically illustrate a cross-section of an example of a culture additive diffusion mechanism 23. The entire periphery of an additive retention unit 20 may be surrounded by a diffusion adjustment unit 22, as illustrated in FIG. 1B, or the periphery may be surrounded by an impermeable unit 41, which blocks diffusion or passage of an additive, and the diffusion adjustment unit 22, as illustrated in FIG. 1A.

(Additive Retention Unit)

The additive retention unit 20 retains additive inside the additive retention unit 20 so that additive does not diffuse to the outside of the additive retention unit 20 without passing through the diffusion adjustment unit 22. In the present disclosure, stating that the additive does not diffuse refers to a state in which diffusion of the additive is considered to be substantially zero. The additive retention unit 20 may have any specific form. To cause the additive to diffuse gradually to the outside of the additive retention unit 20 via the diffusion adjustment unit 22, a porous material capable of enclosing the additive is preferably included in at least a portion of the additive retention unit 20. The additive retention unit 20 is more preferably entirely formed from porous material 20. The porous material may be a polymer gel, such as a chemical gel based on covalent bonds or a physical gel based on non-covalent intermolecular forces or the like, or may be a polymer gel in which covalent bonds and noncovalent intermolecular forces contribute to formation of the gel structure. Specifically, the following can be used as the porous material: hydrogels formed from sugar chains such as agarose, dextrin, pectin, sodium alginate, and xanthan gum; hydrogels formed from proteins such as collagen, hyaluronic acid, elastin, and gelatin; hydrogels formed from synthetic polymers such as polyacrylamide, polyethylene glycol, and silicone; and inorganic materials such as mesoporous carbon, mesoporous aluminosilicate, and mesoporous silica. A hydrogel is more preferably included in a portion of the additive retention unit, as doing so facilitates formation of pores roughly equivalent to various additives.

The above-described porous material may be appropriately modified by a functional group to increase the affinity for the retained additive. To prevent unwanted diffusion of the additive, the porous material may be modified by a functional group, and the functional group and the additive may be reacted to form a covalent or non-covalent bond, thereby fixing the additive on the porous material. The bond between the functional group and the additive is preferably a non-covalent bond for good diffusion of the additive. Examples of the functional group added to the porous material include hydrophilic groups such as a hydroxyl group, amino group, imino group, sulfone group, active ester group, and carboxyl group; and hydrophobic groups such as an alkyl group, phenyl group, and fluoroalkyl group.

A molecule capable of specifically recognizing and binding to an additive may be bound to the above-described porous material. For example, antibodies and aptamers that specifically bind to specific molecules such as proteins; single-stranded DNA that specifically binds to nucleic acids having a specific base sequence; lectins that specifically bind to sugar chains; and the like may be bound to the porous material. The porous material may also include a molecular imprint material that specifically recognizes an additive.

(Diffusion Adjustment Unit)

The diffusion adjustment unit 22 adjusts the diffusion rate of the additive from the inside of the additive retention unit 20 to the outside of the additive retention unit 20. It suffices to adjust the diffusion rate by a switch between two states, i.e. a state in which diffusion of the additive to the outside of the additive retention unit 20 is encouraged, and a state in which diffusion of the additive to the outside of the additive retention unit 20 is suppressed (including the case of substantially zero diffusion). The diffusion adjustment unit 22 may, for example, control the diffusion rate with a method that uses a physical barrier, such as an electromagnetic valve, or control the diffusion rate with a method that uses a state change of a chemical substance, such as a stimulus-responsive material. The diffusion adjustment unit 22 may also adjust the diffusion rate by changing the affinity between the inner surface of the additive retention unit 20 and the additive.

In an embodiment, the culture additive diffusion mechanism 23 may change the diffusion rate of the additive in accordance with a change in at least one environmental parameter. This configuration enables changing of the diffusion rate of the additive by changing the permeability of the additive with respect to the diffusion adjustment unit 22 or the affinity between the inner surface of the additive retention unit 20 and the additive, or by opening and closing of a valve, such as an electromagnetic valve. This configuration thereby enables addition of the additive with a simple configuration, without the use of a complicated apparatus configuration.

The diffusion adjustment unit 22 is preferably a membrane structure or a valve that includes an environment-responsive material in at least a portion thereof. Examples of the environment-responsive material include a stimulus-responsive material, a shape-memory polymer, a shape-memory alloy, and an elastic body. When an environmental parameter is changed, these environment-responsive materials change structurally, the permeability of the additive with respect to the membrane structure changes, or a member forming a valve changes by deformation such as expansion/contraction or bending to open or close the valve. Consequently, the diffusion rate of the additive changes.

The environment-responsive material may respond to any environmental parameter. However, examples of the environmental parameter include the following: temperature, light, pH, magnetic fields, electric fields, sound waves, redox, molecular concentration, and the like when the environment-responsive material is a stimulus-responsive material; light and temperature when the environment-responsive material is a shape-memory polymer; temperature when the environment-responsive material is a shape-memory alloy; and pressure when the environment-responsive material is an elastic body.

Among the above-described environment-responsive materials, the diffusion adjustment unit 22 particularly preferably includes a stimulus-responsive material. When the diffusion adjustment unit 22 includes a stimulus-responsive material, the stimulus provided to the diffusion adjustment unit 22 can be controlled to change the diffusion rate of the additive, for example by changing the permeability of the additive with respect to the diffusion adjustment unit 22 or changing the affinity between the inner surface of the additive retention unit 20 and the additive. Therefore, as compared to a known technique that requires a complex flow path for controlling addition of the additive, the additive can be added with a simple configuration, without the use of a complicated apparatus configuration.

The diffusion adjustment unit 22 is preferably a membrane structure or a valve that includes a stimulus-responsive material in at least a portion thereof. The stimulus-responsive material may be of any type, and the above-described materials that respond to particular stimuli may be used as appropriate. When these stimulus-responsive materials receive a stimulus and change structurally, the permeability of the additive with respect to the membrane structure changes, or a member forming a valve changes by deformation such as expansion/contraction or bending to open or close the valve. The diffusion rate of the additive can thus be adjusted via the diffusion adjustment unit 22.

In an example, the stimulus-responsive material may be a stimulus-responsive material that changes from an aggregated state to a swollen state in response to a stimulus. A temperature-responsive material, a pH-responsive material, a molecule-responsive material, a light-responsive material, a redox-responsive material, a sound wave-responsive material, and the like can be used as such a stimulus-responsive material.

Among the above-described types of stimulus, local heating of the stimulus-responsive material and thermal diffusion enable a temperature rise around the culture target, such as cells, to be suppressed within a range that substantially has no adverse effect on culturing. Hence, a temperature-responsive material with little adverse effect on cells is preferably used as the stimulus-responsive material. A lower critical solution temperature (LCST)-type polymer and an upper critical solution temperature (UCST)-type polymer, for example, can be used as the temperature-responsive material. In an aqueous solution, an LCST-type polymer is hydrophilic at a temperature equal to or less than the LCST (coiled; swollen state) and undergoes phase transition to become hydrophobic (globular; aggregated state) at a temperature greater than the LCST. In an aqueous solution, a UCST-type polymer is hydrophobic at a temperature less than the UCST (globular; aggregated state) and undergoes phase transition to become hydrophilic (coiled; swollen state) at a temperature equal to or greater than the UCST.

Polyamide-based LCST-type polymers, polyether-based LCST-type polymers, phosphoester-based LCST-type polymers, polymers incorporating proteins, and the like can be used as the above-described LCST-type polymer. In greater detail, poly(N-isopropylacrylamide), poloxamers, poly(N-vinylcaprolactam), poly methyl vinyl ether, methyl cellulose, and elastin-containing polymers reported by Conrad et al. (Conrad et al., (2009)) can be used; and as UCST-type polymers, poly(allylamine-co-allylurea), poly(acrylamide-co-acrylonitrile), hydroxypropyl cellulose, poloxamers such as poloxamer 407, methacrylamide polymers, polymethacrylate having a sulfobetaine group, and the like can be used. These polymers can be used alone, or a plurality thereof can be used in combination. The LCST-type polymer or UCST-type polymer may also be a block copolymer formed using two or more monomers selected from the group consisting of isopropyl acrylamide, caprolactam, allyl amine, allyl urea, sulfobetaine, ethylene glycol, methacrylate, styrene, norbornene, phosphazene, methyl vinyl ether, acrylonitrile, and lactide. The phase transition temperature of these block copolymers can be adjusted by the type and quantity ratio of the monomers that are used. An LCST-type polymer and a UCST-type polymer can be combined and used as a stimulus-responsive material. The phase transition temperature of these temperature-responsive materials can be appropriately adjusted by the amount and the like of a functional group that is introduced. For example, an alkyl group, amide group, piperazine group, pyrrolidine group, acetal group, ketal group, oxazoline group, oxyethylene group, sulfonate group, alcohol group, sulfobetaine group, uracil group, ureido group, glycine amide group, and the like can be used as the functional groups that are introduced. For good control over diffusion of the additive, the phase transition temperature of the temperature-responsive material is preferably within a different temperature range than the culturing temperature. The phase transition temperature of the temperature-responsive material is also preferably a temperature that does not adversely affect culturing. In an example, the phase transition temperature of the temperature-responsive material is preferably in a range from 20° C. to 60° C. When animal cells, such as human cells, are the culture target, the phase transition temperature is preferably 38° C. or more to 50° C. or less to ensure a different temperature range than the culturing temperature of around 37° C.

The change in the diffusion rate of the additive via a membrane structure including a stimulus-responsive material that changes from an aggregated state to a swollen state is explained with reference to FIG. 2. In FIG. 2, an example of a membrane structure that includes an LCST-type polymer or a UCST-type polymer is described. The example in FIG. 2 is an enlarged illustration of a configuration with a membrane structure that includes an LCST-type polymer or a UCST-type polymer as the diffusion adjustment unit 22 at the border between the additive retention unit 20, which retains an additive 38, and the outside of the additive retention unit 20 (in the example in FIG. 2, a culture unit 11 provided in a culture container, described below). In the membrane structure illustrated in FIG. 2, the LCST-type polymer is in an aggregated state (state X) at a temperature higher than the LCST, and the UCST-type polymer is in an aggregated state at a temperature lower than the UCST. The LCST-type polymer undergoes phase transition to a swollen state (state Y) upon the temperature becoming less than the LCST, and the UCST-type polymer undergoes phase transition to a swollen state upon the temperature becoming equal to or greater than the UCST. In the hydrophilic swollen state, the additive 38 inside the additive retention unit 20 can pass through the additive retention unit 20 (membrane structure). The additive 38 therefore diffuses to the outside of the additive retention unit 20 (the inside of the culture unit 11) in accordance with the difference in concentration of the additive 38 between the inside and outside of the additive retention unit 20. The diffusion rate of the additive 38 can thus be changed by temperature control (between two states in the example in FIG. 2, i.e. a state with substantially zero diffusion, and a state in which diffusion occurs).

While not being bound by theory, it is thought that in the swollen state (state Y) of the stimulus-responsive material, the ability of the additive 38 to pass through the additive retention unit 20 (membrane structure) could, for example, (i) enable the additive to pass through a gap in the gel of the stimulus-responsive material forming the additive retention unit 20 (membrane structure) in the swollen state by the gel becoming low density and (ii) enable water molecules that are the driving force of diffusion to pass through the additive retention unit 20 (membrane structure) by the stimulus-responsive material becoming hydrophilic in the swollen state.

Although not illustrated, in the case of using a membrane structure such as the one illustrated in FIG. 2 for the diffusion adjustment unit 22, the culture additive diffusion mechanism 23 is preferably designed by estimating the amount of contraction of the stimulus-responsive material in advance and providing leeway in the swollen state.

As illustrated in FIG. 19, the diffusion adjustment unit 22 may be configured by binding one end of a stimulus-responsive material 49 that reversibly changes from the aggregated state to the swollen state to the additive retention unit 20 and forming a membrane structure to cover the additive retention unit 20. FIG. 19 illustrates an enlargement of a configuration in which one end of the stimulus-responsive material 49 is bound to the additive retention unit 20, which retains the additive 38, and a membrane structure is provided at the border with the outside of the additive retention unit 20 (in the example in FIG. 19, the culture unit 11 provided in a culture container, described below). The stimulus-responsive material 49 in the aggregated state (state X) undergoes phase transition to the swollen state (state Y) in response to a stimulus. In the swollen state, the additive 38 inside the additive retention unit 20 passes through the additive retention unit 20 (membrane structure) to the outside of the additive retention unit 20 (inside the culture unit 11 in the example in FIG. 19). The diffusion rate of the additive 38 can thus be changed with a stimulus.

The change in the diffusion rate of the additive via a valve including a stimulus-responsive material that changes from an aggregated state to a swollen state is now explained. The volume of the stimulus-responsive material changes upon the stimulus-responsive material changing from an aggregated state to a swollen state in response to a stimulus. Consequently, a member forming the valve deforms by expansion/contraction, bending, or the like to open or close the valve, and the diffusion rate of the additive changes.

Polythiamine, for example, can be used as the above-described pH-responsive material. The amino group of a gel including polythiamine is protonated by the pH being lowered, and the main chain becomes rigid, thereby prompting a change from the aggregated state to the swollen state. Hence, using a membrane structure or a valve that includes a pH-responsive material as the diffusion adjustment unit 22 and adjusting the pH outside the diffusion adjustment unit 22 enables adjustment of the diffusion rate of the additive via the diffusion adjustment unit 22.

A gel with fixed molecules having a molecule recognition function, such as lectin, or a gel with a fixed enzyme can be used as the above-described molecule-responsive material. A gel that includes these molecule-responsive materials changes from the aggregated state to the swollen state in accordance with the presence of molecular bonds. Hence, using a membrane structure or a valve that includes a molecule-responsive material as the diffusion adjustment unit 22 and adjusting the molecular concentration outside the diffusion adjustment unit 22 enables adjustment of the diffusion rate of the additive via the diffusion adjustment unit 22.

Examples of the above-described light-responsive material include polymers containing azobenzene groups and cyclodextrin groups, azobenzene-bound polyacrylic acid, and nitrocinnamic acid esterified polyethylene glycol. A gel formed from these light-responsive materials changes from the aggregated state to the swollen state upon irradiation of light having various wavelengths. Hence, using a membrane structure or a valve that includes a light-responsive material as the diffusion adjustment unit 22 and adjusting the irradiation of light onto the diffusion adjustment unit 22 enables adjustment of the diffusion rate of the additive via the diffusion adjustment unit 22.

The stimulus-responsive material may be a redox-responsive material that responds to redox. Examples of the redox-responsive material include polymers and polymer gels in which a host molecule cyclodextrin (CD) and a redox-responsive guest molecule ferrocene (Fc) are introduced into the side chain. These redox-responsive materials change from an aggregated state to a swollen state upon a change in the cross-linking density inside the gel in accordance with redox. Therefore, when using a membrane structure or a valve including a redox-responsive material as the diffusion adjustment unit 22, the redox state of the redox-responsive material can be changed by adjusting the amount of the oxidant and/or reducing agent outside the diffusion adjustment unit 22, or by providing a stimulus such as electric potential. This enables adjustment of the diffusion rate of the additive via the diffusion adjustment unit 22.

The stimulus-responsive material may be a sound wave-responsive material that responds to sound waves. An example of a sound-wave responsive material is an ultrasonic-wave responsive material. The anti-type binuclear palladium complex anti-1a that includes a pentamethylene chain, reported on by Isozaki et al. (Isozaki et al., 2007), can be used as the ultrasonic-wave responsive material. These ultrasonic wave-responsive materials change from the aggregated state to the swollen state in response to irradiation of ultrasonic waves. Hence, using a membrane structure or a valve that includes a sound wave-responsive material as the diffusion adjustment unit 22 and adjusting the irradiation of sound waves onto the diffusion adjustment unit 22 enables adjustment of the diffusion rate of the additive via the diffusion adjustment unit 22.

The stimulus-responsive material may also be an electric field-responsive polymer material that responds to an electric field. Poly(2-acrylamido-2-methylpropanesulfonic methacrylate), for example, can be used as the electric field-responsive polymer material. Poly(2-acrylamido-2-methylpropanesulfonic methacrylate) has a negative charge and interacts electrostatically with the additive. This electrostatic interaction is greatly affected by electric fields. Accordingly, use of a membrane structure containing poly(2-acrylamido-2-methylpropanesulfonic methacrylate) as the diffusion adjustment unit 22 enables adjustment of the permeability of the additive via the membrane structure by application of an electric field and therefore enables adjustment of the diffusion rate.

The stimulus-responsive material may also be a magnetic field-responsive polymer material that responds to a magnetic field. Examples of the magnetic field-responsive polymer material include an elastic material that has magnetic particles mixed therein or fixed thereto. When a valve member that is the diffusion adjustment unit 22 is formed from a gel that contains these magnetic field-responsive polymer materials, the magnetic particles fixed to the inner elastic material are attracted by the magnetic field, causing the valve member to deform by expansion/contraction, bending, or the like and to open or close. Application of a magnetic field thereby enables adjustment of the diffusion rate of the additive via the diffusion adjustment unit 22.

When the stimulus-responsive material is a polymer material, the stimulus-responsive material can, for example, be a linear polymer or a branched polymer. The stimulus-responsive material may also be a cyclic polymer. The molecules of the stimulus-responsive material may be cross-linked. The stimulus-responsive material may form a polymer brush structure. When the molecular size of the additive is small, the stimulus-responsive material is preferably formed to be highly dense by cross-linking, a polymer brush structure, or the like to avoid unnecessary diffusion of the additive.

In addition to the above-described stimulus-responsive materials, the environment-responsive material may include a control signal receiving material that converts a particular control signal into a stimulus to which the stimulus-responsive material responds. When the environment-responsive material includes a control signal receiving material, a particular control signal can be converted into a stimulus to which the stimulus-responsive material responds. This enables control of the diffusion rate by the provision of a particular control signal.

The diffusion adjustment unit 22 is preferably a membrane structure or a valve that includes a stimulus-responsive material and a control signal receiving material in at least a portion thereof. The stimulus-responsive material and the control signal receiving material inside the membrane structure or the valve are configured so that the stimulus-responsive material receives a stimulus emitted by the control signal receiving material. In an example, the stimulus-responsive material and the control signal receiving material are cross-linked. Before the stimulus-responsive material is hardened, the control signal receiving material may be mixed and kneaded, with the stimulus-responsive material subsequently being hardened. This allows the stimulus-responsive material and the control signal receiving material to be formed so that the control signal receiving material cannot diffuse from the stimulus-responsive material.

A control signal receiving material that combines well with the stimulus-responsive material can be selected. For example, a near-infrared absorber that absorbs near-infrared rays and generates heat; magnetic nanoparticles that generate heat upon application of an alternating current magnetic field; a photocatalyst, a representative example of which is titanium oxide that absorbs light and exhibits a redox ability; and the like can be used.

The various stimulus-responsive materials described above can be used as the stimulus-responsive material. Among the above-described stimulus-responsive materials, a stimulus-responsive material that changes from an aggregated state to a swollen state in response to a stimulus is preferred.

Among stimulus-responsive materials that change from an aggregated state to a swollen state, a temperature-responsive material is particularly preferable as the stimulus-responsive material. In an example, the environment-responsive material includes a temperature-responsive material as a stimulus-responsive material and includes a near-infrared absorber that absorbs near-infrared rays as a control signal receiving material. The temperature-responsive material changes the diffusion rate of the additive in accordance with a temperature change of the near-infrared absorber. In this configuration, near-infrared rays are used as the control signal, and the near-infrared absorber is used as the control signal receiving material. The near-infrared absorber absorbs near-infrared rays irradiated as a control signal and emits heat. The structure of the temperature-responsive material near the near-infrared absorber changes due to this heat. For example, the permeability of the additive with respect to the diffusion adjustment unit 22 changes, or a valve opens an closes, enabling a change in the diffusion rate of the additive. The temperature-responsive material has a structure that changes reversibly in accordance with temperature. Therefore, when irradiation of near-infrared rays is stopped, and the near-infrared absorber stops emitting heat, the structure of the temperature-responsive material returns to its original state due to a drop in temperature, and the diffusion rate of the additive returns to its original state. The infrared rays do not adversely affect the culture target, such as cells, and only the area near the near-infrared absorber is heated. The area around the culture target is only heated by heat diffusion within a range with no adverse effect. This configuration therefore enables control of the addition of the additive to the culture target in a less invasive manner.

Wavelengths that water molecules tend not to absorb are preferably used for the near-infrared light. For example, wavelengths of 650 nm or greater to 950 nm or less, 1000 nm or greater to 1350 nm or less, and 1500 nm or greater to 1800 nm or less can be used.

Organic compounds, metal structures, carbon structures, or the like can be used as the near-infrared absorber. A material that tends not to precipitate even when mixed with a temperature-responsive material during production is preferred as the near-infrared absorber, and a material with a large surface area is preferred for efficient absorption of near-infrared rays, making use of a small material preferable.

Among metal structures, metal nanorods are preferred as the near-infrared absorber, since the absorption spectrum can be changed by adjustment of the aspect ratio. Gold nanorods are more preferable in terms of stability. Gold nanorods with a diameter in the transverse direction of approximately 5 nm to 100 nm can be used.

Organic dyes are preferred as an organic compound. Suitable examples of organic dyes include a cyanine dye, phthalocyanine dye, naphthalocyanine compound, nickel dithiolene complex, squaryl dye, quinone compound, diimmonium compound, azo compound, porphyrin compound, dithiol metal complex, naphthoquinone compound, and diimmonium compound.

Resin particles containing an organic dye may be used as the organic compound. The resin containing an organic dye is not limited to being particulate in shape. Having the organic dye be contained in resin can suppress leakage of the organic dye into a culture fluid and is therefore effective for preventing the organic dye from affecting the culture target, such as cells.

Carbon nanotubes, fullerene, carbon nanowire, and the like can suitably be used as carbon structures. Carbon nanotubes with a diameter of approximately 0.4 nm to 50 nm can be used.

These near-infrared absorbers can be used alone, or a plurality thereof can be used in combination.

A suitable functional group may be added by modification to these near-infrared absorbers for cross-linking with the temperature-responsive material. In particular, when a metal structure or a carbon structure is used as the near-infrared absorber, a functional group is preferably added to the surface by modification for cross-linking with the temperature-responsive material. The functional group added to the metal structure may, for example, be a methyl group, amino group, carboxyl group, or the like. The functional group added to the carbon structure may, for example, be a methylol group, nitro group, carboxyl group, acyl chloride group, boronic acid group, or the like.

The diffusion adjustment unit 22 is preferably a membrane structure or a valve that includes a temperature-responsive material and a near-infrared absorber in at least a portion thereof. In an example, a membrane structure or a valve includes a cross-linked body in which a temperature-responsive material and a near-infrared absorber are cross-linked by a cross-linking agent, and a structural change in the cross-linked body due to irradiation of near-infrared rays changes the diffusion rate of the additive.

With reference to FIG. 3, the change in the diffusion rate of the additive via a membrane structure including a stimulus-responsive material, which changes from an aggregated state to a swollen state, and a control signal receiving material is explained. FIG. 3 illustrates an example in which transmission of near-infrared rays to a membrane structure including a temperature-responsive material and a near-infrared absorber yields a change in the diffusion rate of an additive via the membrane structure. The example in FIG. 3 is an enlarged illustration of a configuration with a membrane structure that includes a UCST-type polymer and a near-infrared absorber 39 as the diffusion adjustment unit 22 at the border between the additive retention unit 20, which retains the additive 38, and the outside of the additive retention unit 20 (in the example in FIG. 3, a culture unit 11 provided in a culture container, described below). While not illustrated, the near-infrared absorber 39 and the UCST-type polymer are cross-linked. As illustrated in FIG. 2, the UCST-type polymer included in the membrane structure is in an aggregated state (state X) at a temperature lower than the UCST. When near-infrared rays (control signal 34) are irradiated on this membrane structure, the near-infrared absorber 39 absorbs the near-infrared rays and generates heat. The temperature around the near-infrared absorber 39 then locally rises. When the temperature becomes equal to or greater than the UCST due to this temperature rise, the UCST-type polymer undergoes a phase transition to the swollen state (state Y). In the hydrophilic swollen state, the additive 38 inside the additive retention unit 20 can pass through the additive retention unit 20 (membrane structure). The additive 38 therefore diffuses to the outside of the additive retention unit 20 (the inside of the culture unit 11) in accordance with the difference in concentration of the additive 38 between the inside and outside of the additive retention unit 20. The diffusion rate of the additive 38 can thus be changed by irradiation of infrared rays.

While not illustrated, the membrane structure may include an LCST-type polymer. Contrary to the aforementioned case, irradiation of near-infrared rays causes the LCST-type polymer included in the membrane structure to undergo a phase transition from the swollen state (state Y) to the aggregated state (state X) in this case, enabling the diffusion rate of the additive 38 to be changed.

As illustrated in FIG. 20, the diffusion adjustment unit 22 may be configured by binding one end of a stimulus-responsive material 49 that reversibly changes from the aggregated state to the swollen state to the additive retention unit 20, binding the other end to a control signal receiving material (the near-infrared absorber 39 in the example in FIG. 20), and forming a membrane structure to cover the additive retention unit 20. FIG. 20 illustrates an enlargement of a configuration in which one end of the stimulus-responsive material 49 is bound to the additive retention unit 20, which retains the additive 38, the other end is bound to a control signal receiving material (the near-infrared absorber 39 in the example in FIG. 20), and a membrane structure is provided at the border with the outside of the additive retention unit 20 (in the example in FIG. 20, the culture unit 11 provided in a culture container, described below). When the control signal 34, such as near-infrared rays, is irradiated onto the membrane structure, the control signal receiving material (the near-infrared absorber 39 in the example in FIG. 20) receives the control signal 34 and converts the control signal 34 to a stimulus to which the stimulus-responsive material 49 responds. The stimulus-responsive material 49 in the aggregated state (state X) receives the stimulus converted by the control signal receiving material and undergoes phase transition to the swollen state (state Y). In the swollen state, the additive 38 inside the additive retention unit 20 passes through the additive retention unit 20 (membrane structure) to the outside of the additive retention unit 20 (inside the culture unit 11 in the example in FIG. 19). The diffusion rate of the additive 38 can thus be changed with a stimulus.

Figure 1C:
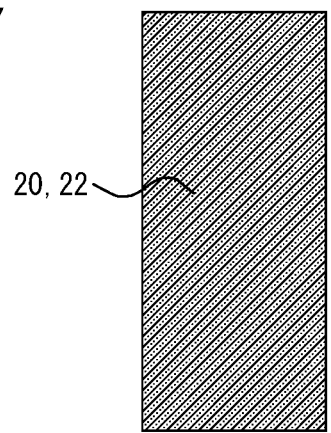

The additive retention unit 20 and the diffusion adjustment unit 22 may include the same material. In an embodiment, the culture additive diffusion mechanism 23 includes a stimulus-responsive material that changes from the aggregated state to the swollen state in response to a stimulus, as illustrated in FIG. 1C. By the additive being directly carried by the stimulus-responsive material, the stimulus-responsive material can be caused to function both as the additive retention unit 20 and the diffusion adjustment unit 22. Provision of a stimulus to the culture additive diffusion mechanism 23 causes the stimulus-responsive material to change from the aggregated state to the swollen state. At the time of this change, the additive that was carried by the stimulus-responsive material in the aggregated state can diffuse from the stimulus-responsive material in the swollen state. Diffusion of the additive can thus be controlled by a stimulus. Formation of the additive retention unit 20 and the diffusion adjustment unit 22 from the same material in this way can facilitate production of the culture additive diffusion mechanism 23.

Alternatively, in the embodiment in FIG. 1C, the culture additive diffusion mechanism 23 may include, as the stimulus-responsive material, an electric field-responsive polymer material that responds to an electric field, and the additive may be enclosed in the electric field-responsive polymer material to combine the functions of the additive retention unit 20 and the diffusion adjustment unit 22. Poly(2-acrylamido-2-methylpropanesulfonic methacrylate), for example, can be used as the electric field-responsive polymer material. Poly(2-acrylamido-2-methylpropanesulfonic methacrylate) has a negative charge and interacts electrostatically with the additive. This electrostatic interaction is greatly affected by electric fields. Hence, when the additive is enclosed in an electric field-responsive polymer material such as poly(2-acrylamido-2-methylpropanesulfonic methacrylate), the electrostatic interaction between the additive and the electric field-responsive polymer material can be changed by application of an electric field, and the diffusion coefficient diffusion resistance of the additive can be changed, enabling adjustment of the rate of diffusion of the additive from the culture additive diffusion mechanism 23.

In the present embodiment, the above-described temperature-responsive material, pH-responsive material, molecule-responsive material, light-responsive material, redox-responsive material, sound wave-responsive material, and the like can suitably be used as a stimulus-responsive material that changes from the aggregated state to the swollen state in response to a stimulus. In the present embodiment, the culture additive diffusion mechanism 23 may include a control signal receiving material in addition to the stimulus-responsive material. Details of the stimulus-responsive material and the control signal receiving material are as above and are therefore omitted here.

(Impermeable Unit)

The impermeable unit 41 does not diffuse or transmit the additive. The impermeable unit 41 may have any specific form but is preferably formed from a material that does not have affinity with the additive. The impermeable unit 41 is, for example, formed from an organic material such as a hydrophobic polymer or an inorganic material such as a metal thin film. In an embodiment for adjusting the diffusion rate with the control signal 34, the impermeable unit 41 is preferably formed from a non-hydrophobic polymer, as this configuration does not block the control signal 34. The surface of the porous material used as the additive retention unit 20 may be cross-linked to form the impermeable unit 41.

While not illustrated, the surface on the outer side of the additive retention unit 20 may be covered with a different material from the material forming the additive retention unit 20. Covering the surface on the outer side of the additive retention unit 20 with a different material from the material forming the additive retention unit 20 can prevent adsorption of components in the additive or the culture medium on the impermeable unit 41, leakage of components of the additive retention unit 20 into the culture medium, and the like.

FIGS. 1A to 1C illustrate examples of the culture additive diffusion mechanism 23 having an overall rectangular shape, but the overall shape of the culture additive diffusion mechanism 23 is not limited to being rectangular. For example, the overall shape of the culture additive diffusion mechanism 23 may be spherical. The culture additive diffusion mechanism 23 is particularly easy to produce when the overall shape of the culture additive diffusion mechanism 23 is spherical. For example, a spherical culture additive diffusion mechanism 23 with the form illustrated in FIG. 1B or FIG. 1C can be produced, without use of a mold, to have an overall spherical shape by a method for dripping a material solution into a liquid (liquid drip method).

(Additive)

The additive can be selected in accordance with the culture target and the purpose of culturing. Examples include low molecular weight compounds, nucleic acids, lipids, proteins, sugars, and amino acids. Proteins known to function as biological signals, such as differentiation-inducing factors, cell growth factors, antibodies, hormones, and chemokines, can be used as additives. Low molecular weight compounds that can be used as additives include inhibitors, antibiotics, and the like that bind to oxygen, receptors, and the like to impede the activity thereof. Such additives may be materials chemically synthesized artificially or may be materials obtained naturally. Depending on the culture protocol, a surfactant may also be used as an additive. The additive may be vesicles, such as exosomes and liposomes, that include a plurality of components; biomaterial extracts; and cell secretions. The additive is not limited to a chemical substance and may be a virus.

Apart from the additive itself being retained in the additive retention unit 20, a cell-free protein synthesizing system may be enclosed in the additive retention unit 20, and proteins synthesized by the synthesizing system may be added as an additive. The cell-free protein synthesizing system may include translation components, such as ribosomes, tRNA, aminoacyl tRNA synthetases, translation initiation factors, translation elongation factors, and translation termination factors, and additionally amino acids, energy molecules such as ATP and GTP, salts such as magnesium ions, and templates such as DNA or mRNA. In the present embodiment, these can be used as additives when the protein has low stability or when the protein is difficult to isolate.

Microbes or animal cells may be enclosed in the additive retention unit 20, and secretions from the microbes or the animal cells may be added as an additive. In the present embodiment, these can be used as additives when the secretion has low stability or when the secretion is difficult to isolate. Furthermore, even when the added component is unknown, microbes or animal cells that secrete the component can be enclosed in the additive retention unit 20 for suitable addition of the component as an additive.

The aforementioned additives can be added alone, or a plurality thereof can be added in combination. When a plurality of additives are added in combination, a plurality of additives may be retained in one additive retention unit 20, or as described below, a plurality of culture additive diffusion mechanisms 23 may be provided for one culture container, and various types of additives may be retained in cell retention units of the plurality of culture additive diffusion mechanisms 23.

(Culture Target)

Any culture target can be cultured using the culture additive diffusion mechanism 23. Cells can suitably be cultured as the culture target. Either adhesive cells or floating cells can be cultured. The cells may be any of unicellular organisms, animal cells, plant cells, insect cells, or tumor cells. The cells may also be stem cells or cells derived from organs. Examples of stem cells include iPS cells, ES cells, mesenchymal stem cells, hematopoietic stem cells, neural stem cells, and Muse cells.

The culture additive diffusion mechanism 23 can be used not only to culture single cells, but also to culture tissue formed by a plurality of cells gathering together and to culture multi-cellular microbes.

<Cell Culture Carrier>

In an embodiment, the culture additive diffusion mechanism is a cell culture carrier for culturing cells and carries additive, which is an agent, on a cell culture stimulus-responsive substrate that includes a stimulus-responsive polymer material, made of a polymeric stimulus-responsive material, and a control signal receiving material.

In the cell culture carrier of the present embodiment, the additive is carried by the cell culture stimulus-responsive substrate. Before a control signal is received, the stimulus-responsive polymer material in the cell culture stimulus-responsive substrate is aggregated in the cell culture carrier. The polymer is highly dense and highly hydrophobic in this aggregated state and therefore has low solubility in water. Hence, the carried additive does not diffuse outside of the carrier but rather continues to be carried. The additive is in a stored state in the cell culture carrier.

When a control signal is received, the aggregated stimulus-responsive polymer material in the cell culture stimulus-responsive substrate relaxes. The solubility in water therefore increases, the material swells, and the carried additive diffuses outside the carrier. Furthermore, when input of the control signal stops, the cell culture stimulus-responsive substrate returns to the aggregated state, and diffusion of the additive stops. Aggregation of the stimulus-responsive polymer material can be reversibly controlled by controlling input of the control signal. In other words, the cell culture carrier of the present embodiment enables detailed control of diffusion of an additive by control of the input of a control signal.

The cell culture carrier of the present embodiment is described below in detail.

First, a first embodiment of a cell culture carrier is described.

Figure 21:
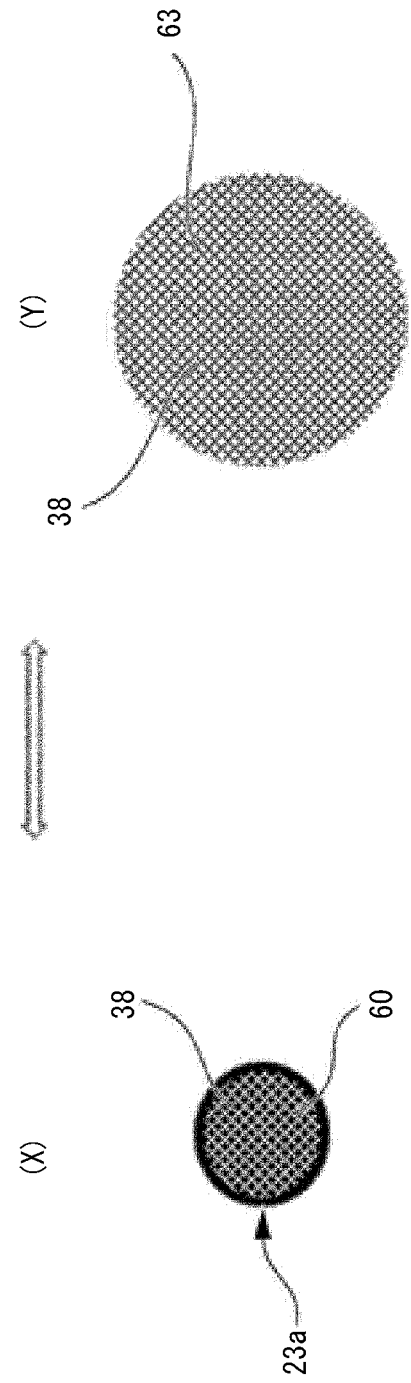
FIG. 21 schematically illustrates an example of a cell culture carrier.

FIG. 21 schematically illustrates a cross-section of a cell culture carrier 23a of the first embodiment. In the cell culture carrier 23a illustrated in FIG. 21, an additive 38 is carried on a cell culture stimulus-responsive substrate 60. When the additive 38 is carried directly on the cell culture stimulus-responsive substrate 60, the structure is simplified, enabling efficient production. The input of a control signal to the cell culture carrier 23a leads to a swollen state 63 of overall swelling.

The reference sign (X) in FIG. 21 is the state in which the stimulus-responsive polymer material is aggregated and diffusion of the additive is stopped. The reference sign (Y) in FIG. 21 is the state in which the stimulus-responsive polymer material is swollen and the additive can diffuse. In the present embodiment, the additive can be reversibly controlled between the diffusion state (Y) and suspension of diffusion (X) by control of input of the control signal. (X) and (Y) indicate the same states in the drawings below.

For example, when the state before input of the control signal is the aggregated state indicated by the reference sign (X), and the control signal is received, then the stimulus-responsive polymer material in the cell culture stimulus-responsive substrate 60 enters a non-aggregated state 63 (or a swollen state), and solubility in water increases. The carried additive 38 thereby diffuses outside the carrier.

As another example, when the state before input of the control signal is the non-aggregated state indicated by the reference sign (Y), and the control signal is received, then the stimulus-responsive polymer material in the cell culture stimulus-responsive substrate 60 enters the aggregated state, and solubility in water decreases. The carried additive 38 is thereby retained inside the carrier.

—Stimulus-Responsive Polymer Material

The structure of the stimulus-responsive polymer material changes in response to an external stimulus, and the permeability of the additive changes. The stimulus-responsive polymer material may be a linear polymer or a branched polymer. The stimulus-responsive polymer material may be used after the molecules thereof are cross-linked. A polymer brush structure using the stimulus-responsive polymer material may be used. When the molecular size of the additive is small, the stimulus-responsive polymer material is preferably highly dense due to cross-linking, a polymer brush structure, or the like to improve sealing efficiency.

Materials that respond to various stimuli, such as temperature, light, pH, magnetic fields, electric fields, ultrasonic waves, redox, molecular concentration, and the like can suitably be used as the stimulus-responsive polymer material. In the present embodiment, a temperature-responsive polymer material is preferably used, since this material can converge to the culturing temperature by thermal equilibrium even when locally heated and does not adversely affect cells by virtue of having little effect on the culture environment.

Polymers that respond to biological conditions, such as lower critical solution temperature (LCST)-type poly(N-isopropylacrylamide), upper critical solution temperature (UCST)-type poly(allylamine-co-allylurea), poly(acrylamide-co-acrylonitrile), or the like can be used as the temperature-responsive polymer material. The stimulus-responsive temperature is preferably in a range from 20° C. to 60° C. In particular, when culturing animal cells such as human cells, the stimulus-responsive temperature is preferably 38° C. or more to 50° C. or less, since the culturing temperature is 37° C. LCST-types and UCST-types can be used separately for reversible control of the states (X) and (Y) before and after input of the control signal.

—Control Signal

The control signal is preferably a magnetic field or light, as these do not require wires. The light is preferably near-infrared light, which tends not to affect cells. In particular, 650 nm or more to 950 nm or less is preferable, 1000 nm or more to 1350 nm or less is more preferable, and 1500 nm or more to 1800 nm or less is preferable, as water molecules tend not to absorb these wavelengths.

—Control Signal Receiving Material

The control signal receiving material may be determined appropriately by the combination of the control signal and the stimulus-responsive polymer material. For example, when the control signal is near-infrared light and the stimulus-responsive polymer material is a temperature-responsive polymer material, organic materials and inorganic materials that can efficiently convert near-infrared light to heat are used in the control signal receiving material. Examples of such materials include organic compounds, fine metal structures, and carbon microstructures, i.e. fine carbon structures.

The use of such materials as the control signal receiving material allows a signal to be received and the area around the control signal receiving material to be heated locally, causing the structure of the temperature-responsive polymer material to change. Diffusion and suspension of diffusion of the additive can thus be controlled reversibly.

—Organic Compound

In the present embodiment, organic dyes are preferred as an organic compound. Examples of organic dyes include a cyanine dye, phthalocyanine dye, naphthalocyanine compound, nickel dithiolene complex, squaryl dye, quinone compound, diimmonium compound, azo compound, porphyrin compound, dithiol metal complex, naphthoquinone compound, and diimmonium compound.

—Metal Structure

In the present embodiment, the metal structure is preferably metal nanorods, which allow control of the absorption wavelength of light by the aspect ratio. Gold nanorods are particularly preferable.

—Carbon Material

The carbon material is preferably a carbon microstructure, i.e. a fine carbon structure. Examples of carbon microstructures include carbon nanotubes, fullerene, and carbon nanowire.

When the control signal uses a magnetic field, the control signal receiving material preferably uses a magnetic material, such as magnetic nanoparticles. An AC magnetic field load causes magnetic nanoparticles to generate heat.

Various functional groups and cross-linking agents that react with the functional groups can be used to join the stimulus-responsive polymer material and the control signal receiving material, to cross-link the molecules of the stimulus-responsive polymer material, and to fix the cell culture stimulus-responsive substrate and the additive.

In the present embodiment, the cross-linking agent may be a homobifunctional cross-linking agent, a heterobifunctional cross-linking agent, or a three or more multifunctional cross-linking agent.

If the functional group is a primary amine, a cross-linking agent including NHS ester, carbodiimide, aldehyde, isothiocyanate, isocyanate, acyl azide, sulfonyl chloride, glyoxal, epoxide, oxirane, carbonate, aryl halide, imide ester, anhydride, fluoroester, or the like can be used.

If the functional group is a carboxyl group, then carbodiimide or the like can be used.

If the functional group is a sulfhydryl group, then a cross-linking agent including maleimide, haloacetic acid, pyridyl disulfide, thiosulphone, vinyl sulfone, or the like can be used.

If the functional group is an aldehyde group, then a cross-linking agent including hydrazide, alkoxyamine, or the like can be used. If the functional group is an aldehyde group, then a cross-linking agent including hydrazide, alkoxyamine, or the like can be used.

A light-responsive group, such as diazirine or aryl azide, may also be used. Chemoselective ligation between azide-alkyne, between azide-phosphine, or the like may be used. Molecules such as polyethylene glycol or DNA may be used as a spacer.

Various materials may be activated by providing the energy of electron beam irradiation or the like and may then be used for binding or cross-linking.

—Additive

In the present embodiment, any of the following may be used as the additive 38 without any particular restrictions: a protein such as an enzyme, a cytokine, a differentiation-inducing factor, or an antibody; a peptide such as a hormone; an antibiotic; a low molecular weight compound such as an amino acid, glucose, or retinoic acid; a nucleic acid such as DNA; nanoparticles; liposomes; or the like.

Next, a second embodiment of a cell culture carrier is described.

Figure 22:
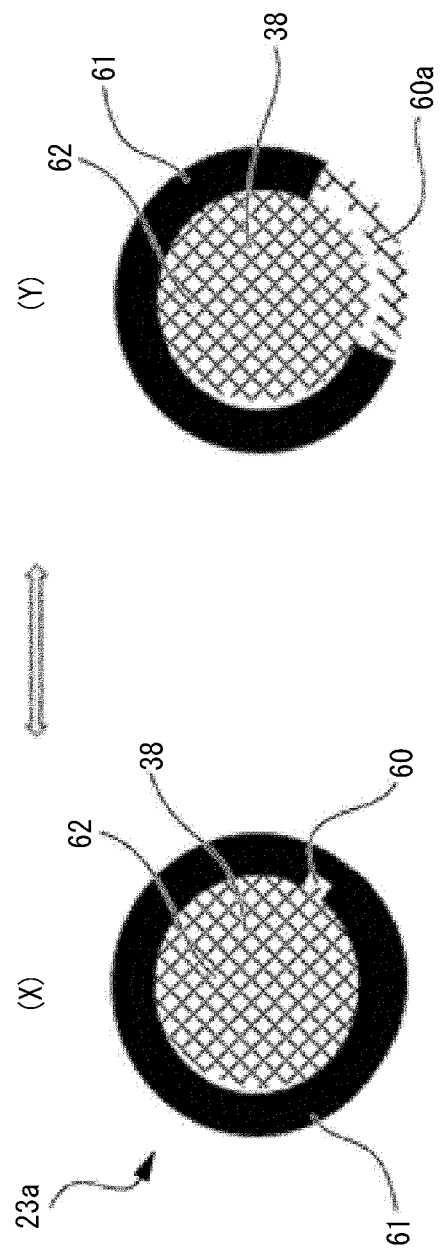
FIG. 22 schematically illustrates an example of a cell culture carrier.

FIG. 22 schematically illustrates a cross-section of a cell culture carrier 23a of the second embodiment. The cell culture carrier 23a illustrated in FIG. 22 includes a cell culture stimulus-responsive substrate 60, a porous material 62, an additive 38, and an additive impermeable layer 61 that is an impermeable unit. The additive 38 is enclosed in the porous material 62. In the present embodiment, a portion of the porous material 62 that includes the additive 38 is covered by the cell culture stimulus-responsive substrate 60, and the remainder is covered by the additive impermeable layer 61. The additive impermeable layer 61 is preferably a hydrophobic polymer, and the additive 38 preferably is not emitted from the portion not covered by the cell culture stimulus-responsive substrate 60. It suffices for the additive impermeable layer 61 to be impermeable and non-adsorptive with respect to the additive. Apart from a hydrophobic polymer, an inorganic material such as a metal thin film may be used, and the porous material may be cross-linked by a cross-linking agent. As necessary, a coating for hydrophilization or the like may be provided.

Adjustment of the location where the cell culture stimulus-responsive substrate 60 is disposed and of the covered area enables control of the diffusion amount and diffusion direction of the additive 38 to achieve the desired supply.

As illustrated in (Y) of FIG. 22, only the location where the cell culture stimulus-responsive substrate 60 is disposed adopts a swollen state 60a upon input of a control signal to the cell culture carrier 23a. Since the additive 38 is only emitted by diffusion from the portion that adopts the swollen state 60a, the diffusion amount and diffusion direction of the additive 38 can be controlled to achieve the desired supply.

—Porous Material

In the present embodiment, the additive 38 is enclosed in a substrate. The substate is preferably a porous material. Hydrogels such as agarose gel and polyacrylamide gel; and inorganic materials such as mesoporous carbon, mesoporous aluminosilicate, and mesoporous silica can be used as the porous material.

In the present embodiment, the additive 38 is preferably enclosed in the porous material 62.

Next, a third embodiment of a cell culture carrier is described.

Figure 23:
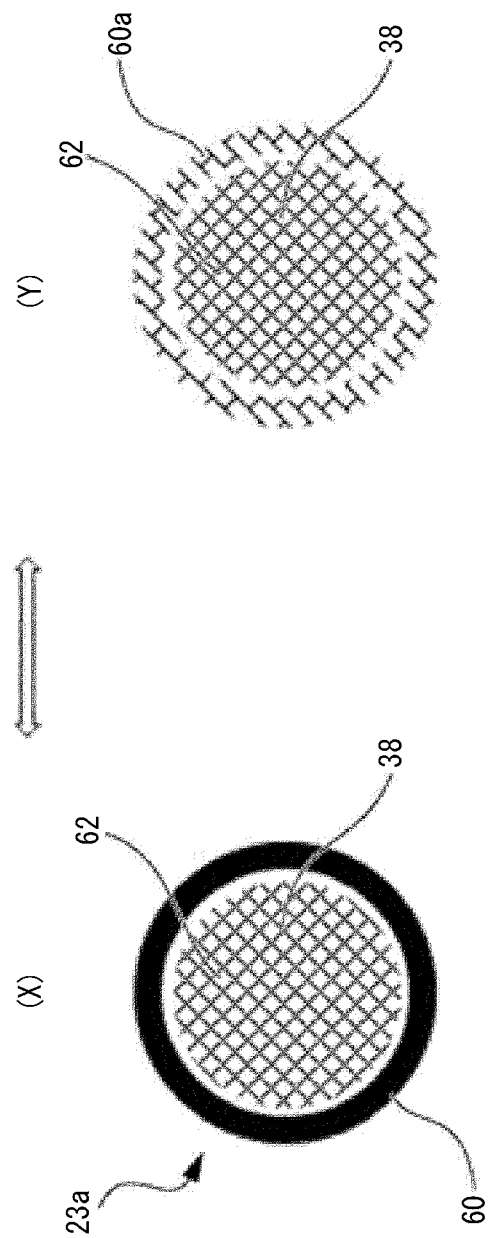
FIG. 23 schematically illustrates an example of a cell culture carrier.

FIG. 23 schematically illustrates a cross-section of a cell culture carrier 23a of the third embodiment. The cell culture carrier 23a illustrated in FIG. 23 includes a cell culture stimulus-responsive substrate 60, a porous material 62, and an additive 38. The additive 38 is enclosed in the porous material 62. In the cell culture carrier 23a of the present embodiment, the additive 38 is covered by and stored in the cell culture stimulus-responsive substrate 60.

The reference sign (X) in FIG. 23 is the state in which the stimulus-responsive polymer material is aggregated and diffusion of the additive is stopped. The reference sign (Y) in FIG. 23 is the state in which the stimulus-responsive polymer material is swollen and the additive can diffuse. In the present embodiment, the additive can be reversibly controlled between the diffusion state (Y) and suspension of diffusion (X) by control of input of the control signal.

For example, when the state before input of the control signal is the aggregated state indicated by the reference sign (X), and the control signal is received, then the stimulus-responsive polymer material in the cell culture stimulus-responsive substrate 60 enters a non-aggregated state 60a, and solubility in water increases. The carried additive 38 thereby diffuses outside the carrier.

As another example, when the state before input of the control signal is the non-aggregated state indicated by the reference sign (Y), and the control signal is received, then the stimulus-responsive polymer material in the cell culture stimulus-responsive substrate 60 enters the aggregated state, and solubility in water decreases. The carried additive 38 is thereby retained inside the carrier.

—Porous Material

In the present embodiment, the additive 38 is carried on a substrate. The substate is preferably a porous material. Hydrogels such as agarose gel and polyacrylamide gel; and inorganic materials such as mesoporous carbon, mesoporous aluminosilicate, and mesoporous silica can be used as the porous material.

In the present embodiment, the additive 38 is preferably enclosed in the porous material 62.

Next, a fourth embodiment of a cell culture carrier is described.

Figure 24:
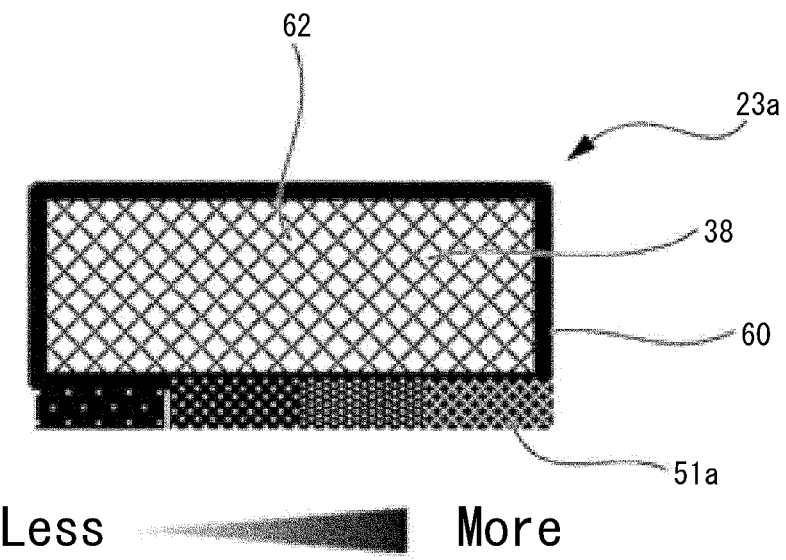
FIG. 24 schematically illustrates an example of a cell culture carrier.

FIG. 24 schematically illustrates a cross-section of a cell culture carrier 23a of the fourth embodiment. In the cell culture carrier 23a illustrated in FIG. 24, a cell culture stimulus-responsive substrate 60 has a control signal receiving material blended therein to form a concentration distribution and is covered by a porous material 62 including an additive 38. Reference sign 51a indicates the gradient of the concentration distribution. Provision of the concentration distribution enables variation in the diffusion rate of the additive 38 with respect to input of the same control signal. Therefore, the concentration distribution of the additive 38 can be controlled spatially inside the below-described cell culture container.

Next, a fifth embodiment of a cell culture carrier is described.

Figure 25:
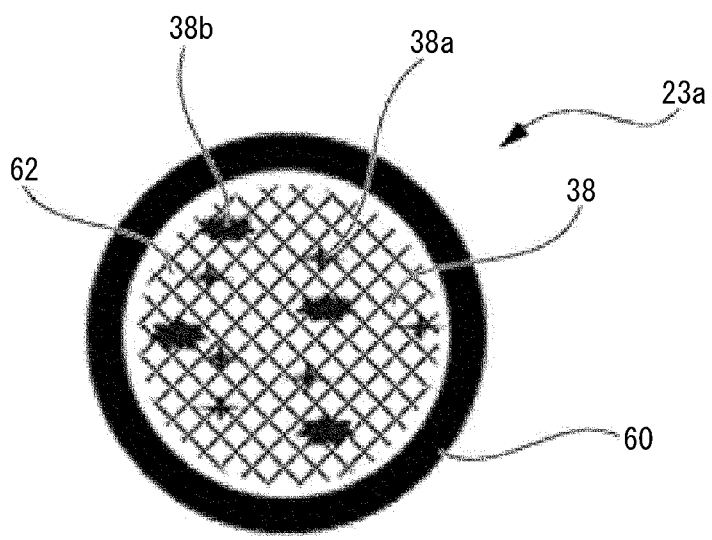
FIG. 25 schematically illustrates an example of a cell culture carrier.

FIG. 25 schematically illustrates a cross-section of a cell culture carrier 23a of the fifth embodiment. In the cell culture carrier 23a illustrated in FIG. 25, an additive 38 is covered by a cell culture stimulus-responsive substrate 60. The additive 38 is enclosed in the porous material 62. A plurality of types of additive 38a and additive 38b are mixed and stored in the additive 38.

Next, a sixth embodiment of a cell culture carrier is described.

Figure 26:
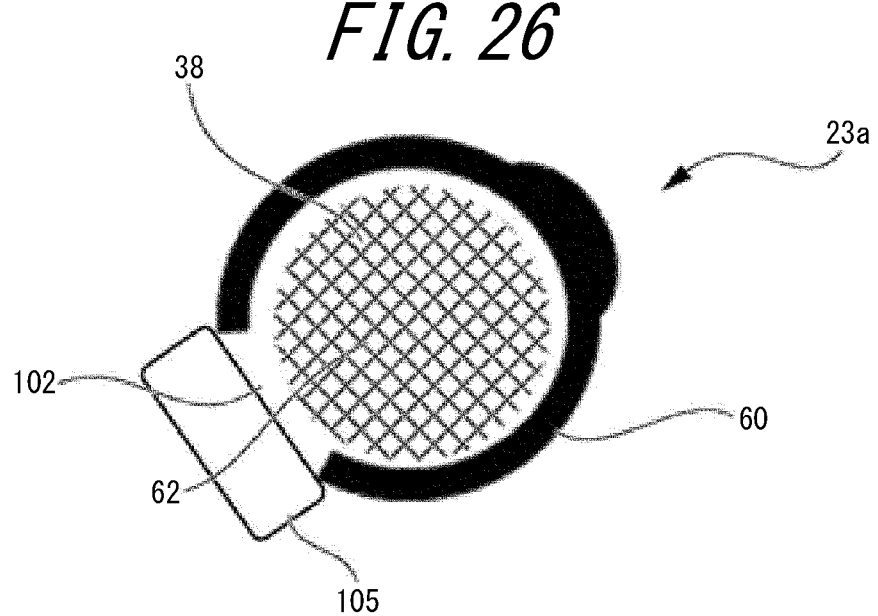
FIG. 26 schematically illustrates an example of a cell culture carrier.

FIG. 26 schematically illustrates a cross-section of a cell culture carrier 23a of the sixth embodiment. In the cell culture carrier 23a illustrated in FIG. 26, a porous material 62 including an additive is covered by a cell culture stimulus-responsive substrate 60. The cell culture carrier 23a includes an injection port 102 on the surface, through which a desired additive 38 can be injected. After injection of the additive, the injection port 102 is sealed by a sealing unit 105 formed by an additive impermeable material, such as a hydrophobic polymer. The effect of reducing leakage of the additive 38 is thereby obtained.

[Culture Container]

Figure 4:
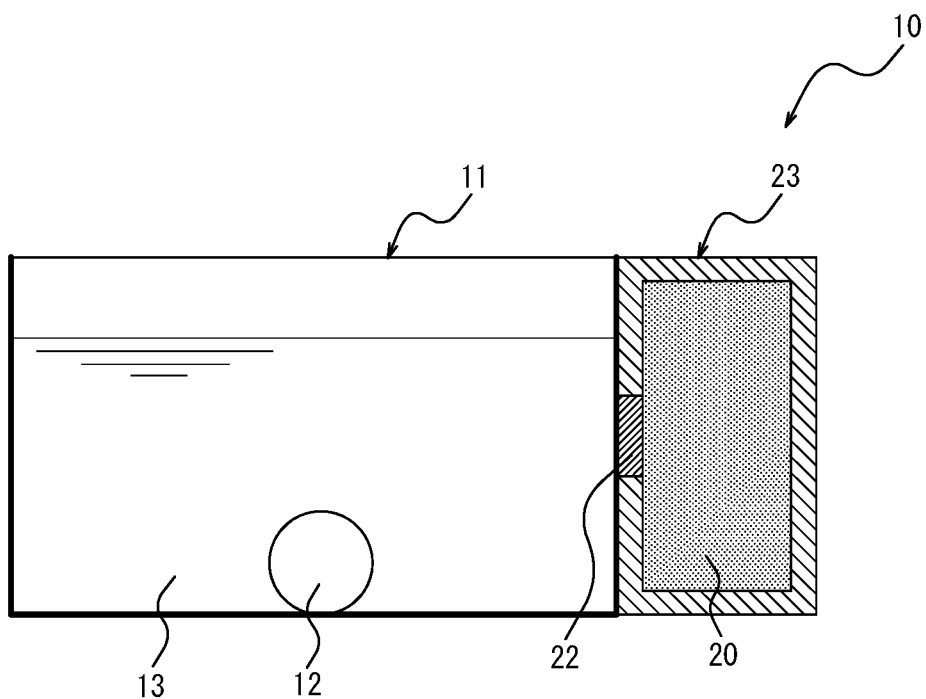
FIG. 4 schematically illustrates an example of an embodiment of a culture container.

FIG. 4 schematically illustrates an example of a culture container. As illustrated in FIG. 4, a culture container 10 includes the above-described culture additive diffusion mechanism 23 and a culture unit 11 into which a culture target 12, such as cells, and a culture medium 13 are introduced. During culturing, as illustrated in FIG. 4, the diffusion adjustment unit 22 is in contact with the culture medium 13. When the culture medium 13 is in liquid form (culture fluid), the culture fluid penetrates into the diffusion adjustment unit 22 from the culture unit 11 and wets the additive retention unit 20, enabling diffusion of the additive from the additive retention unit 20 to the culture medium 13. Hence, by the diffusion adjustment unit 22 adjusting the diffusion rate of the additive from inside the additive retention unit 20 to outside the additive retention unit 20, addition of the additive to the culture medium 13 can be controlled efficiently and easily. This culture container 10 enables cell culturing while efficiently and easily adjusting the addition of additive to the culture medium 13. While not illustrated, a lid may be provided as appropriate on the culture unit 11.

The culture additive diffusion mechanism 23 may be located at any position inside the culture container 10. During culturing, however, the diffusion adjustment unit 22 needs to be in contact with the culture medium 13. The culture additive diffusion mechanism 23 may be configured not to be removable from the culture container 10, or the culture additive diffusion mechanism 23 may be an exchangeable member that can be removed from the culture container 10. When the culture additive diffusion mechanism 23 is an exchangeable member that can be removed from the culture container 10 in this way, the culture container 10 can easily be configured in accordance with the purpose of culturing.

The culture unit 11 can be configured in the same way as a typical culture container in accordance with the purpose of culturing. Any material may be used in the culture unit 11, such as plastic or glass. The culture unit 11 may be coated to prevent adsorption of the additive. This configuration can reduce the loss due to the additive being adsorbed on the culture unit 11. The culture unit 11 may also be made more useful by being disposable.

The culture medium 13 introduced into the culture unit is not restricted and may be selected in accordance with the type of cells or the purpose of culturing. For example, a well-known culture medium, such as a MEM culture medium, DMEM culture medium, RPMI-1640 culture medium, or the like may be used. Culture mediums being developed and used by specific groups as reported in known articles may also be used. An additive that does not require detailed control of addition may be mixed into the culture medium in advance and used. The culture medium may be a liquid or a gel.

When the culture medium is a gel, the diffusion adjustment unit 22 is, for example, immersed in advance in a biocompatible liquid, such as a culture fluid or physiological saline. By the diffusion adjustment unit 22 being immersed in advance in a biocompatible liquid, the liquid penetrates the diffusion adjustment unit 22 and wets the additive retention unit 20, allowing the additive to diffuse suitably from the additive retention unit 20 to the culture medium 13.

The basic configuration of the culture container 10 has been described, but the culture container 10 may also be configured as described below.

Figure 5A:
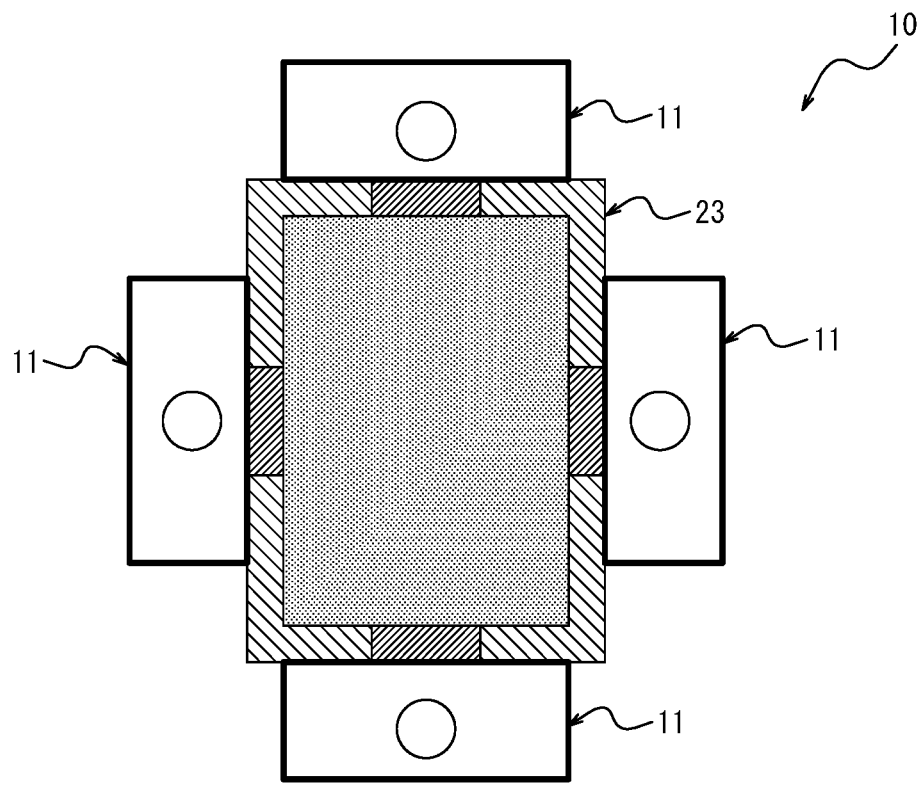
FIGS. 5A and 5B schematically illustrate an example of a culture container that includes a plurality of culture units, where

FIG. 5A schematically illustrates another embodiment of a culture container. FIG. 5A is an overview of an example of a culture container 10 according to the present embodiment as seen from above. As illustrated in FIG. 5A, the culture container 10 may include a plurality of culture units 11. When one culture container 10 includes a plurality of the culture units 11, cells can be cultured simultaneously in the plurality of culture units 11. Cells can thereby be mass-produced efficiently.

As illustrated in FIG. 5A, the plurality of culture units 11 in an example are disposed to surround the culture additive diffusion mechanism 23. For the additive to diffuse into the culture units 11, a plurality of diffusion adjustment units 22 are disposed in the culture additive diffusion mechanism 23 to be in contact with the culture medium introduced in each culture unit 11. Specifically, the culture container 10 illustrated in FIG. 5A includes a plurality (four in the illustrated example) of culture units 11 and a culture additive diffusion mechanism in which a plurality (the same number as the number of culture units 11) of diffusion adjustment units are provided for one additive retention unit. The additive retention units and the culture units 11 are in contact via the diffusion adjustment unit 22.

Figure 5B:
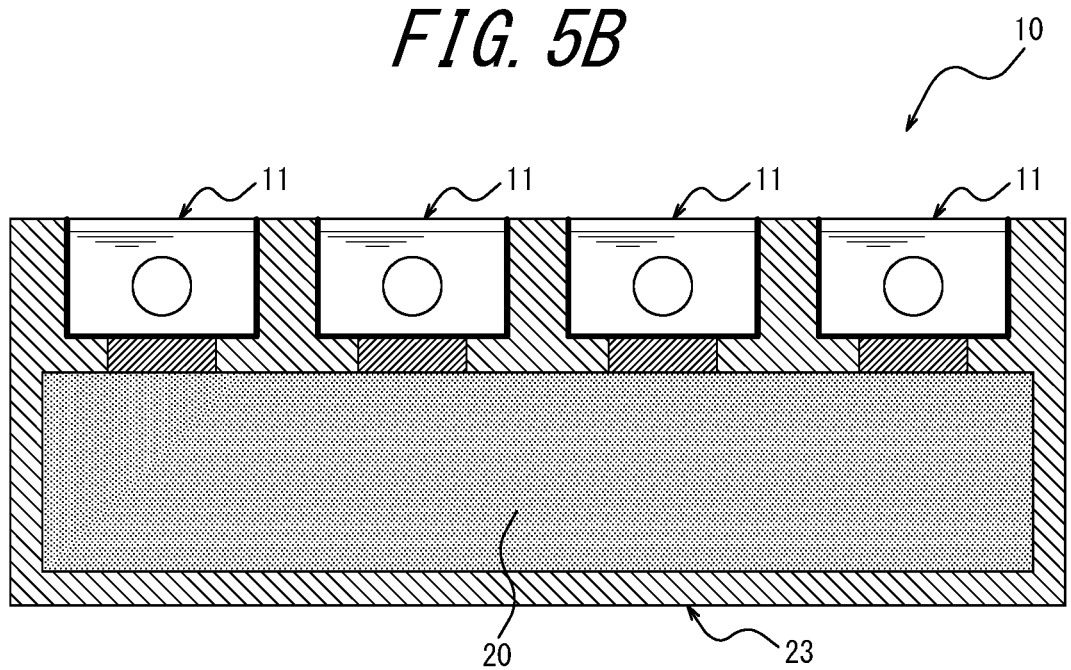

FIG. 5B schematically illustrates a cross-section of another example of the culture container 10. As illustrated in FIG. 5B, the plurality of culture units 11 may be provided on one side of the culture additive diffusion mechanism 23.

Figure 6:
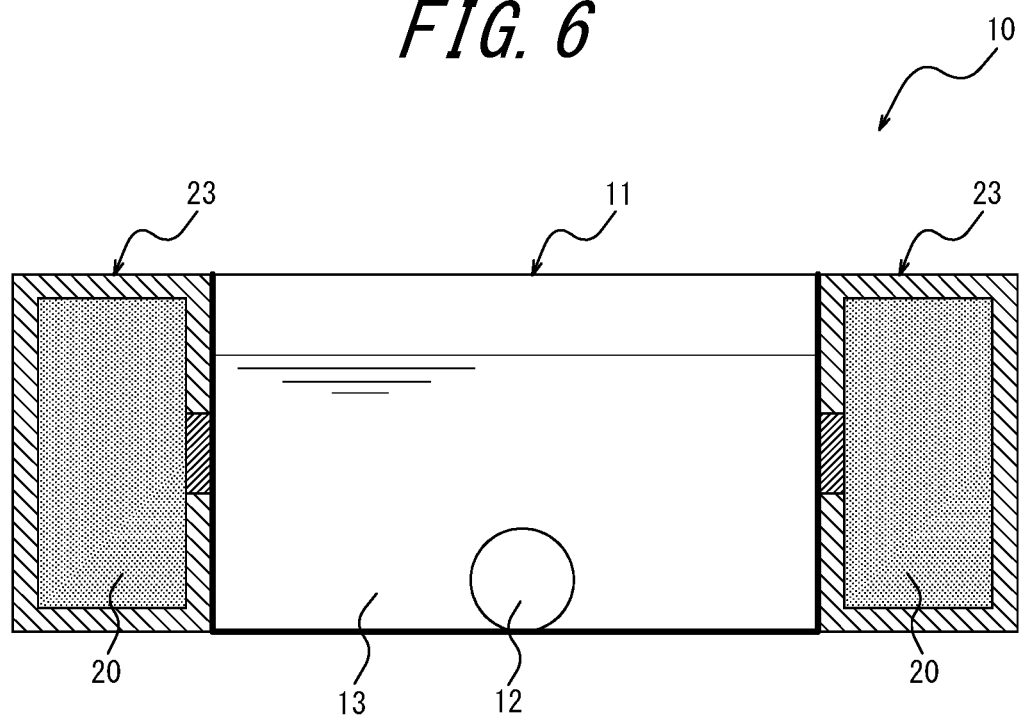
FIG. 6 schematically illustrates an example of a culture container that includes a plurality of additive diffusion mechanisms.

FIG. 6 schematically illustrates another embodiment of a culture container 10. As illustrated in FIG. 6, the culture container 10 may include a plurality of culture additive diffusion mechanisms 23 for one culture unit 11. When the culture container 10 includes a plurality of culture additive diffusion mechanisms 23, addition of the additive from the plurality of culture additive diffusion mechanisms 23 can be controlled independently. This enables addition of the additives to be controlled more freely.

When the culture container 10 includes a plurality of culture additive diffusion mechanisms 23 as illustrated in FIG. 6, the plurality of culture additive diffusion mechanisms 23 may retain different types of additives. Such a plurality of culture additive diffusion mechanisms 23 that retain different types of additives enables independent control of the addition of a plurality of types of additives. This is useful when it is necessary to add a plurality of types of additives at independent times.

Figure 7:
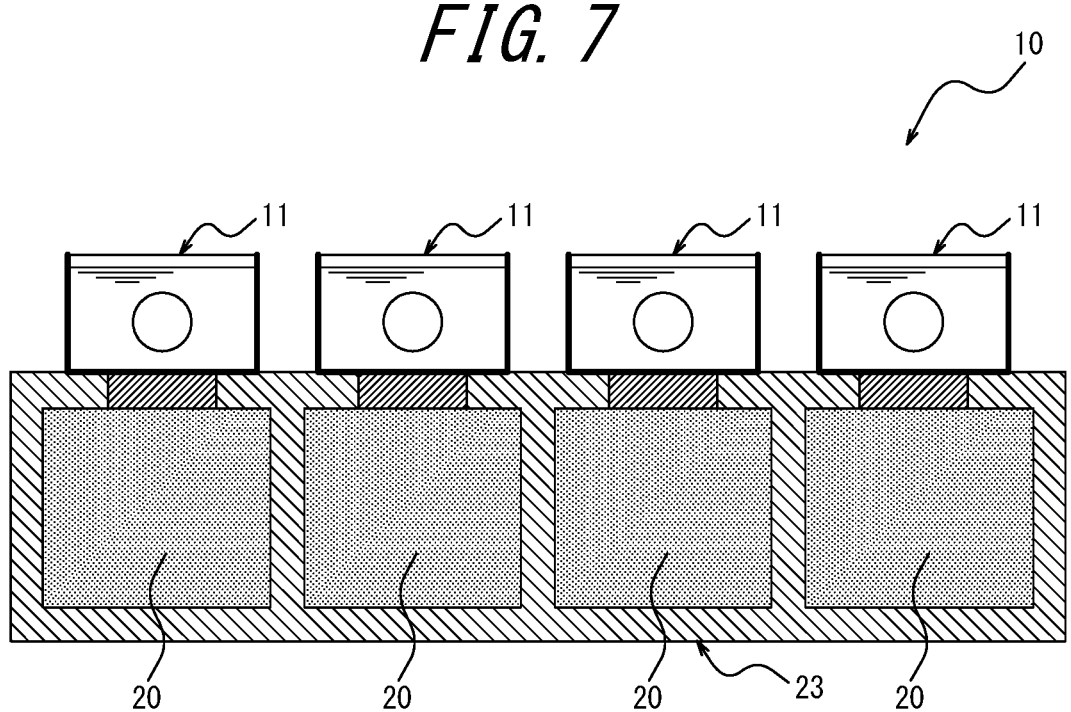
FIG. 7 schematically illustrates an example of a culture container that includes a plurality of culture units and additive diffusion mechanisms.

FIG. 7 schematically illustrates a cross-section of another embodiment of the culture container 10. As illustrated in FIG. 7, the culture container 10 may include a plurality of culture units 11, and one or more (one in the illustrated example) culture additive diffusion mechanisms 23 may be provided for each culture unit 11. Such inclusion of one or more culture additive diffusion mechanisms 23 for each culture container 10 facilitates parallel culturing under a plurality of types of culture conditions.

Figure 8:
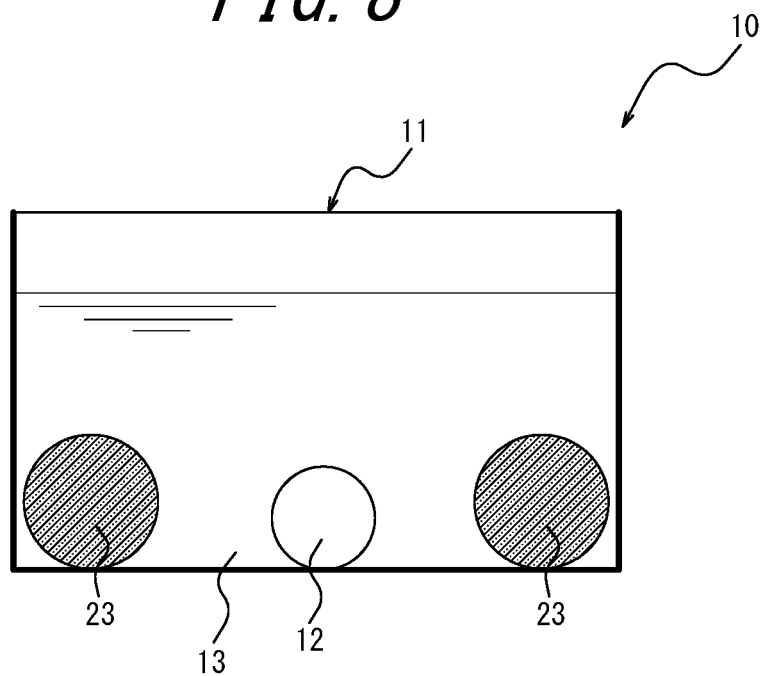
FIG. 8 schematically illustrates an example of a culture container that includes a spherical additive diffusion mechanism.

FIG. 8 schematically illustrates a cross-section of another embodiment of the culture container 10. As illustrated in FIG. 8, the culture additive diffusion mechanism 23 may be disposed at a predetermined position inside the culture unit 11 without being fixed to the culture container 10. The culture additive diffusion mechanism 23 may be spherical, for example, and may be placed inside the culture unit 11 or caused to float. The culture additive diffusion mechanism 23 may be structured to have any of the forms illustrated in FIGS. 1A to 1C, with a spherical configuration. The number of culture additive diffusion mechanisms 23 and the type of additive retained therein may be selected in accordance with the purpose of culturing. When the culture additive diffusion mechanism 23 is disposed inside the culture unit 11 as necessary in this way without being fixed to the culture container 10, the culture container 10 can easily be configured in accordance with the purpose of culturing.

Figure 18:
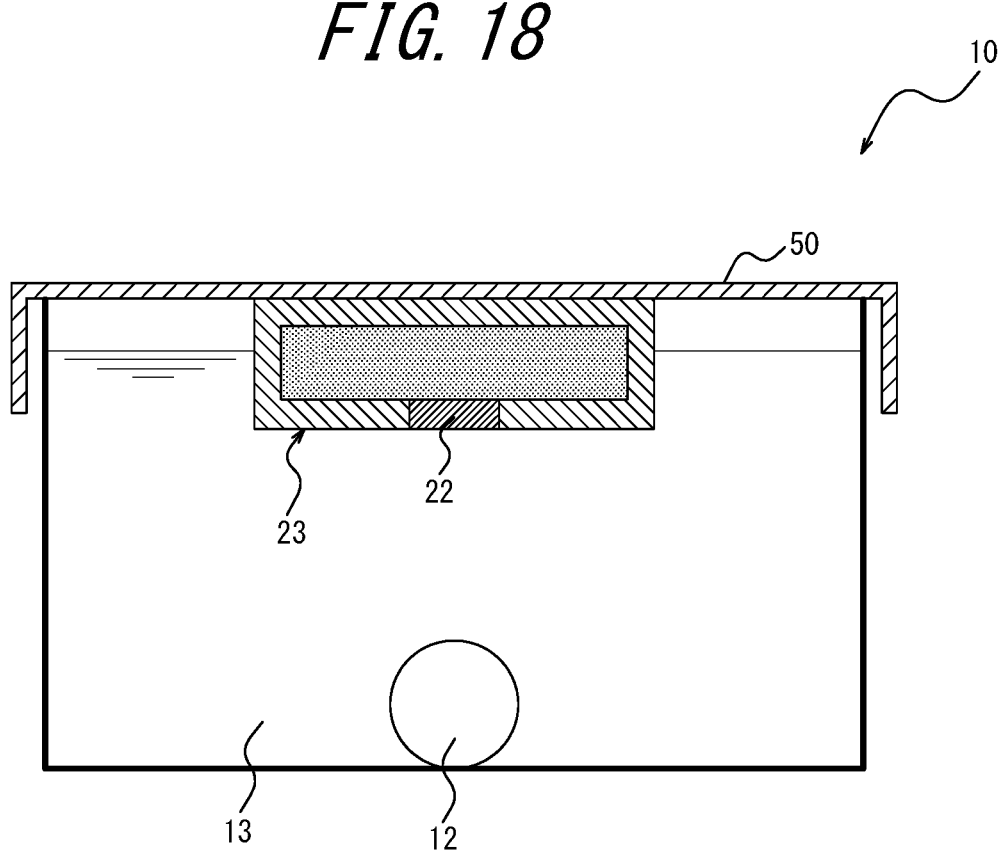
FIG. 18 schematically illustrates an example of a culture container that includes an additive diffusion mechanism disposed on the inside of the lid.

FIG. 18 schematically illustrates a cross-section of another embodiment of the culture container 10. As illustrated in FIG. 18, the culture additive diffusion mechanism 23 may be provided on the inner side of a lid 50 provided in the culture unit 11 (culture unit inner side). The culture medium 13 is introduced to be in contact with the diffusion adjustment unit 22. When the culture additive diffusion mechanism 23 is provided on the inner side of the lid 50 in this way, the culture container 10 can easily be configured in accordance with the purpose of culturing. Furthermore, the present embodiment facilitates production of the culture container 10, since the culture container 10 can be configured by replacing the lid of a typical culture container with the lid 50 that has the culture additive diffusion mechanism 23 provided on the inner side thereof.

Another embodiment of a culture container is described below.

The culture container of the present embodiment is a cell culture container for culturing cells and includes the above-described cell culture carrier and a cell culture unit that is a culture unit for culturing cells.

FIG. 27A schematically illustrates a cross-section of an example cell culture container 10a of the present embodiment. The cell culture container 10a includes a cell culture unit 11a and cell culture carriers 23a, 23b. The cell culture unit 11a includes a cell housing 2.

A well-known material, such as a known culture dish, culture plate well, Lab-on-a-chip, or the like can be used in the cell housing 2. The surface of the cell housing 2 may be coated for adhesion or separation of cells, to prevent non-specific adsorption of proteins, or the like.

Together with the cell culture container 10a of the present embodiment, a cell culture method using the cell culture container 10a of the present embodiment is also described.

In the cell culture container 10a illustrated in FIG. 27A, the cell culture carrier indicated by reference sign 23a is caused to carry a cell trigger factor 38c as an additive, and the cell culture carrier indicated by reference sign 23b is caused to carry a growth factor 38d as an additive.

Next, as illustrated in FIG. 27B, a suspension 6a is introduced into the cell housing 2 using a pipette 6. Subsequently, as illustrated in FIG. 27C, the cell culture unit 11a is covered with the lid 50, and cells are cultured. Cells then adhere to the cell housing 2 as illustrated in FIG. 27D to form a cell population 8.

The cell culture carrier indicated by reference sign 23a includes gold nanorods, having an absorption peak at a wavelength around 780 nm, as a control signal receiving material. The cell culture carrier indicated by reference sign 23b includes gold nanorods, having an absorption peak at a wavelength around 900 nm, as a signal control signal receiving material.

As illustrated in FIG. 27E, when 780 nm near-infrared light A is irradiated as a control signal, the cell trigger factor 38c diffuses from the cell culture carrier indicated by reference sign 23a, and diffusion stops when irradiation is suspended.

As illustrated in FIG. 27F, the cell population 8 moves in the direction of the reference sign 23a due to diffusion of the cell trigger factor 38c.

As illustrated in FIG. 27G, when 900 nm near-infrared light B is irradiated as a control signal, the growth factor 38d diffuses from the cell culture carrier indicated by reference sign 23b, and diffusion stops when irradiation is suspended.

The cells grow due to diffusion of the growth factor 38d.
—Cells

The cells that are the culture target may be stem cells, such as mesenchymal stem cells, ES cells, or iPS cells; differentiated cells of the liver or the like; or an established cell line derived from a tumor or the like. The cells may also be cells other than mammalian cells. The cells may be bacteria, yeast, or fungus.

«Other Embodiments of Cell Culture Container»

Figure 28:
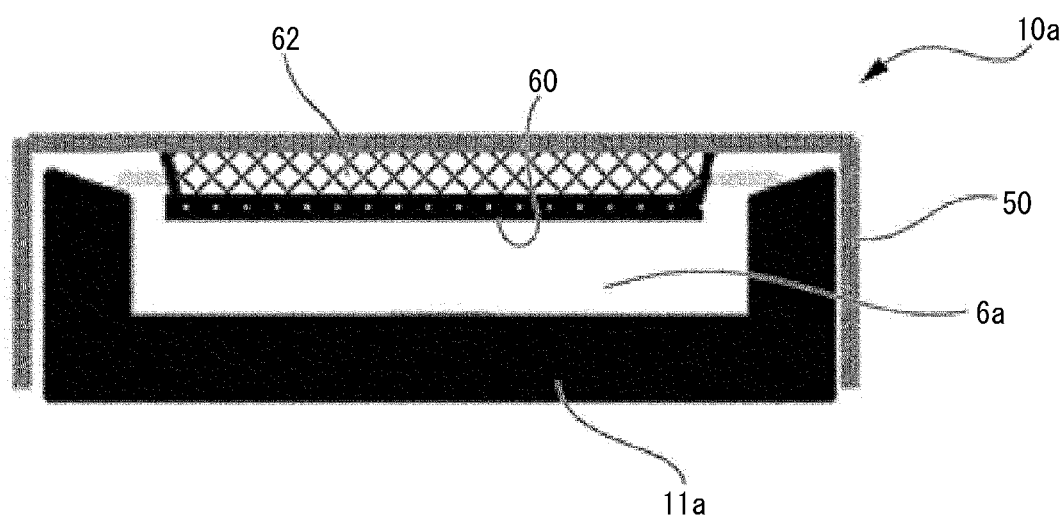
FIG. 28 schematically illustrates an example of a cell culture container.

FIG. 28 illustrates an embodiment of a cell culture container. A cell culture container 10a includes a cell culture stimulus-responsive substrate 60 and a porous material 62, which includes an additive, on the container inner side of the lid 50. The porous material 62 is disposed to be in contact with the lid 50, and the cell culture stimulus-responsive substrate 60 is disposed to touch a cell suspension 6a inside a cell culture unit 11a.

The additive included in the porous material 62 may exhibit a concentration gradient inside the porous material 62. The additive can be supplied by a control signal being inputted from the lid 50 side of the cell culture container 10a.

Figure 29:
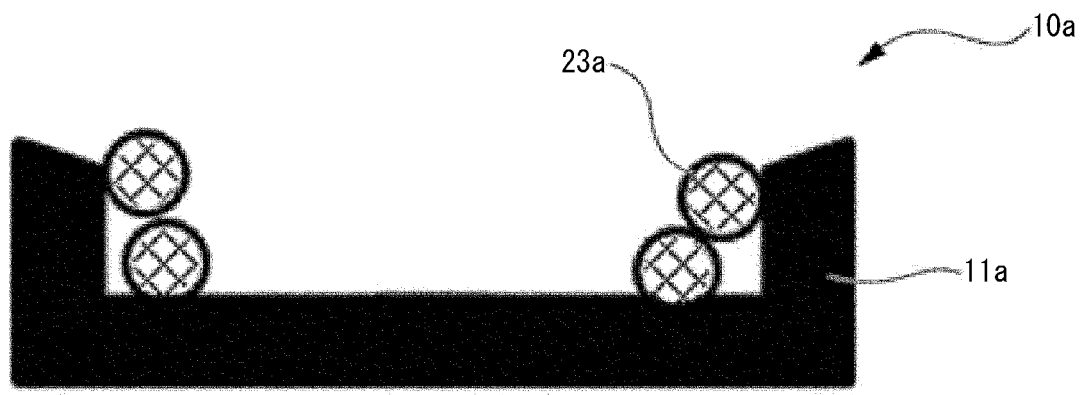
FIG. 29 schematically illustrates an example of a cell culture container.

FIG. 29 illustrates an embodiment of a cell culture container. A cell culture container 10a includes a plurality of bead-shaped cell culture carriers 23a arranged in a cell culture unit 11a. Various types of additives can be supplied by the cell culture carriers 23a carrying different additives.

Figure 30:
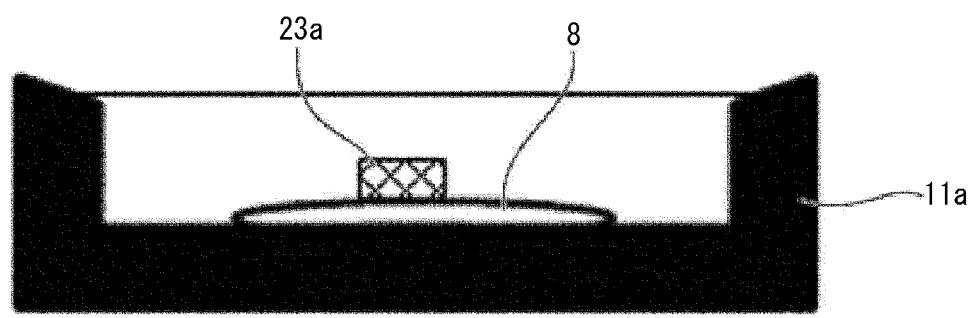
FIG. 30 schematically illustrates an example of a cell culture container.

FIG. 30 illustrates an embodiment of a cell culture container. A cell culture carrier 23a may be placed on top of a cell population 8 when disposed in a cell culture unit 11a.

Figure 31:
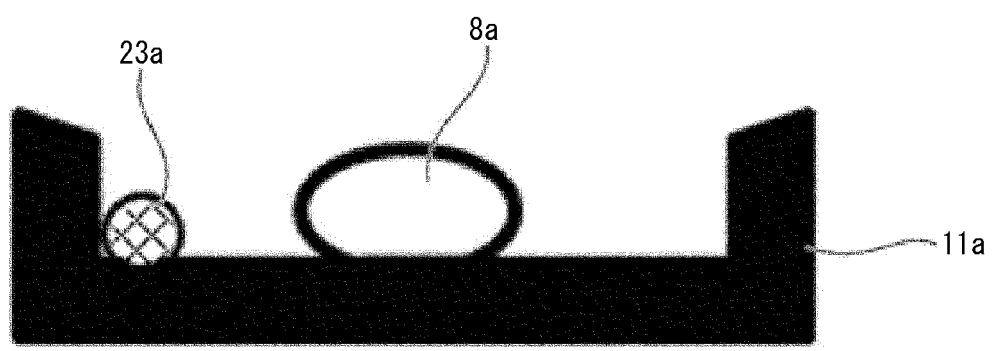
FIG. 31 schematically illustrates an example of a cell culture container.
Figure 32:
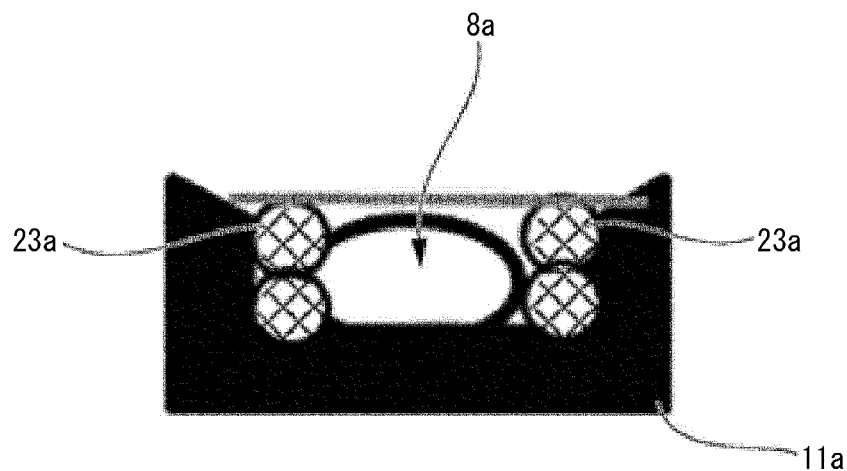
FIG. 32 schematically illustrates an example of a cell culture container.

FIG. 31 illustrates an embodiment of a cell culture container. A cell population may be a three-dimensional cell population 8a located inside a cell culture unit 11a. The cell culture carrier 23a need not be in contact with the three-dimensional cell population 8a. As illustrated in FIG. 32, a plurality of cell culture carriers 23a may be in contact with the three-dimensional cell population 8a.

Figure 33:
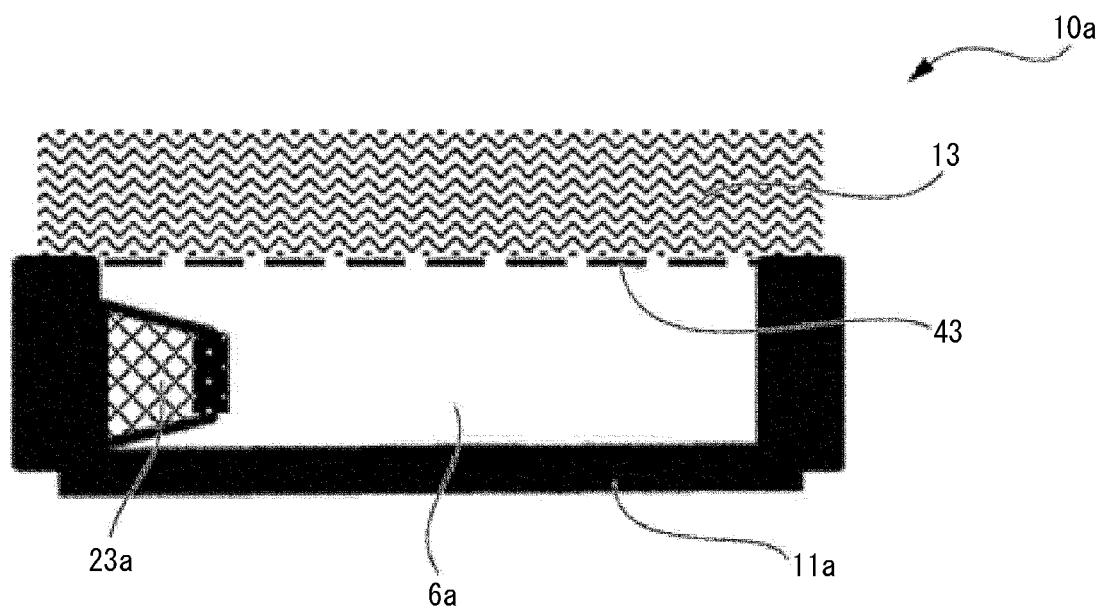
FIG. 33 schematically illustrates an example of a cell culture container.

FIG. 33 illustrates an embodiment of a cell culture container. A cell culture container 10a includes a cell culture unit 11a; a cell culture carrier 23a; a semi-permeable membrane unit 43, which includes a semi-permeable membrane; a culture medium 13; and a cell suspension 6a. The culture medium 13 flows over the semi-permeable membrane unit 43. The present embodiment allows small molecules, such as nutrients and waste products, to be exchanged via the semi-permeable membrane. The environment inside the cell culture unit 11a can thus be maintained in a state suitable for survival of cells. Furthermore, since the culture medium 13 flows over the semi-permeable membrane unit 43, the culture medium need not be exchanged. Polymer materials that cannot pass through the semi-permeable membrane can be supplied by being carried by the cell culture carrier 23a.

Figure 34:
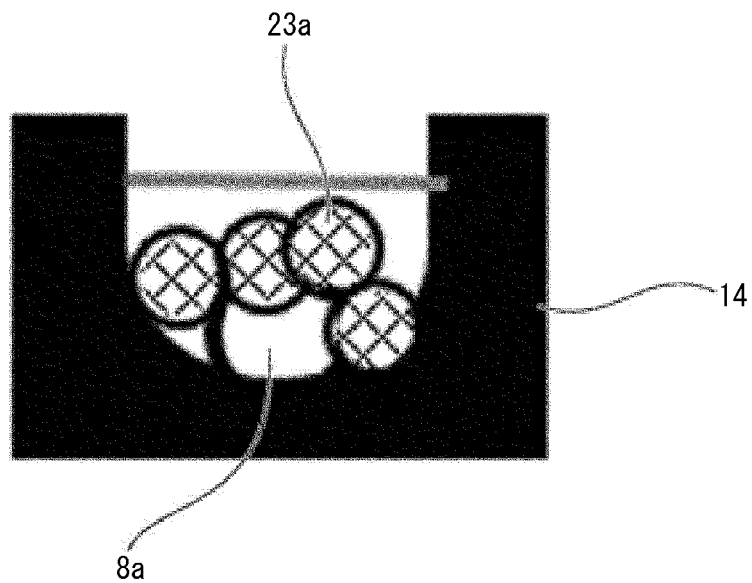
FIG. 34 schematically illustrates an example of a cell culture container.

FIG. 34 illustrates an embodiment of a cell culture container. A cell housing 14 has a concave bottom. When the concave shape of the cell housing 14 is used to form a three-dimensional cell population 8a, continuous stimulation from the cell culture carrier 23a becomes possible.

Figure 35:
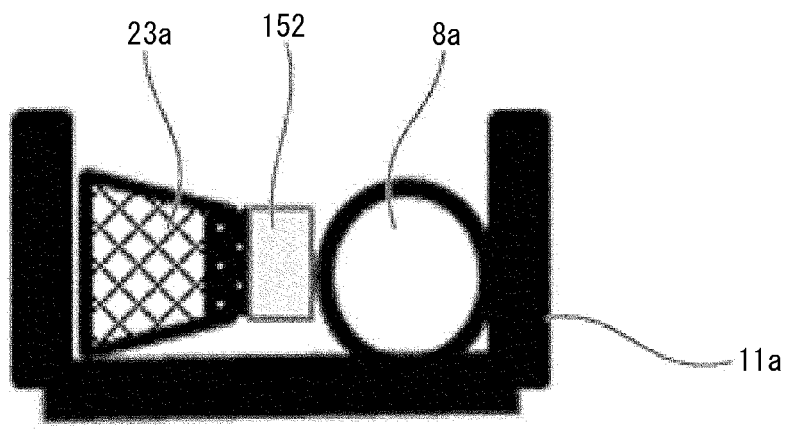
FIG. 35 schematically illustrates an example of a cell culture container.

FIG. 35 illustrates an embodiment of a cell culture container. A spacer layer 152 is provided between a three-dimensional cell population 8a and a cell culture carrier 23a located inside a cell culture unit 11a. This makes the cells less likely to be affected by heating during input of a control signal.

By virtue of containing little other than the culture space, the cell culture container of the present embodiment can secure a wide culture space to culture a large quantity of cells. The cell culture container does not have a complex structure and therefore is inexpensive to produce. Additionally, parameters such as the addition amount of the additive, the timing of addition, and the type can be controlled in detail by adjusting input of a control signal.

The cell culture container of the present embodiment is suitable for producing cells for regenerative medicine products, which require highly efficient mass production by culturing with a complicated protocol over an extended period of time.

For example, differentiation of IPS cells into hepatocytes requires long-term culturing, lasting 30 days or longer, while changing among approximately 3 to 5 types of cytokines daily. In the case of a transplant for liver failure, approximately $10^9$ to $10^{10}$ cells are calculated to be required. Efficient cell production at high density is therefore desired. The cell culture container of the present embodiment does not include wiring and flow paths as essential components. Rather, with a simple mechanism, this cell culture container can comply with a complicated protocol requiring various additives and can achieve mass culturing.

[Culture System]

Figure 9:
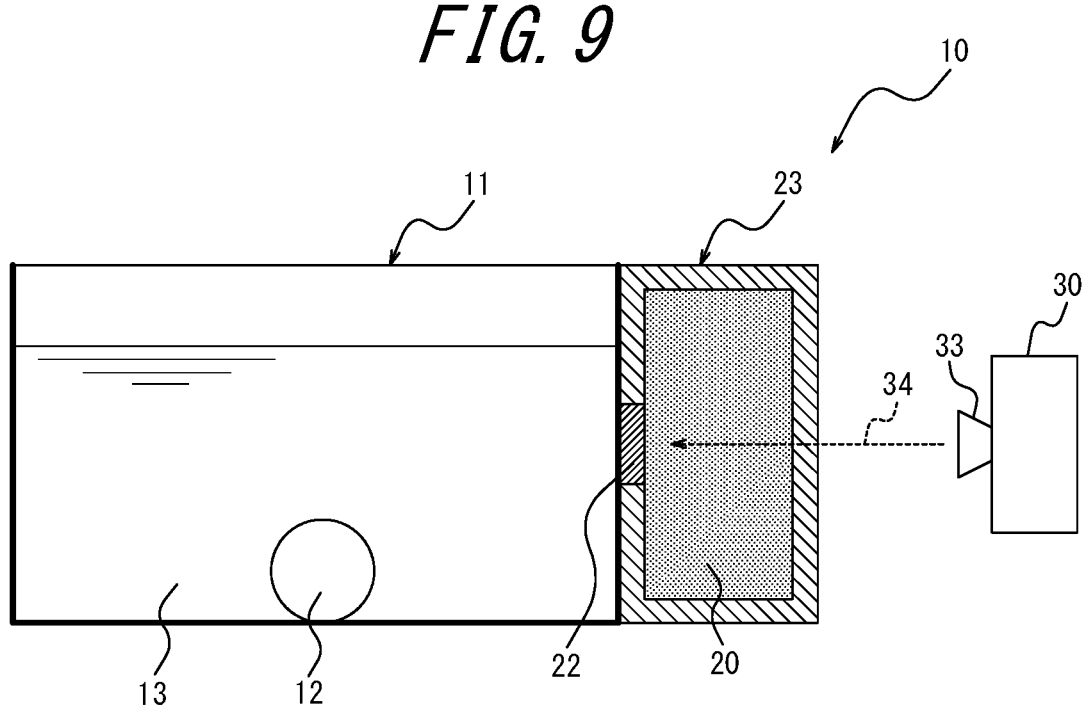
FIG. 9 illustrates the schematic configuration of an example of a culture system.

Next, a culture system using the above-described culture container (cell culture container) of the present disclosure is described. The culture system according to the present disclosure is used for culturing a culture target, such as cells, and enables cell culturing while efficiently and easily controlling the addition of additive to the culture medium 13. FIG. 9 illustrates the schematic configuration of an example of a culture system. As illustrated in FIG. 9, the culture system 100 includes the above-described culture container 10 (cell culture container) and a culture management apparatus 30. From FIG. 9 onwards, cross-sections of the culture container 10 are illustrated schematically. The culture container 10 includes the above-described culture additive diffusion mechanism 23 and culture unit 11, which has culture medium 13 introduced therein and is for culturing cells 12. The culture additive diffusion mechanism 23 includes the additive retention unit 20 for retaining additive and the diffusion adjustment unit 22 that adjusts the diffusion rate of the additive from the inside of the additive retention unit 20 to the outside of the additive retention unit 20. The culture management apparatus 30 includes a transmitter 33 that transmits a control signal 34. The culture additive diffusion mechanism 23 may be the above-described cell culture carrier 23a.

[Configuration of Culture System]

Figure 10:
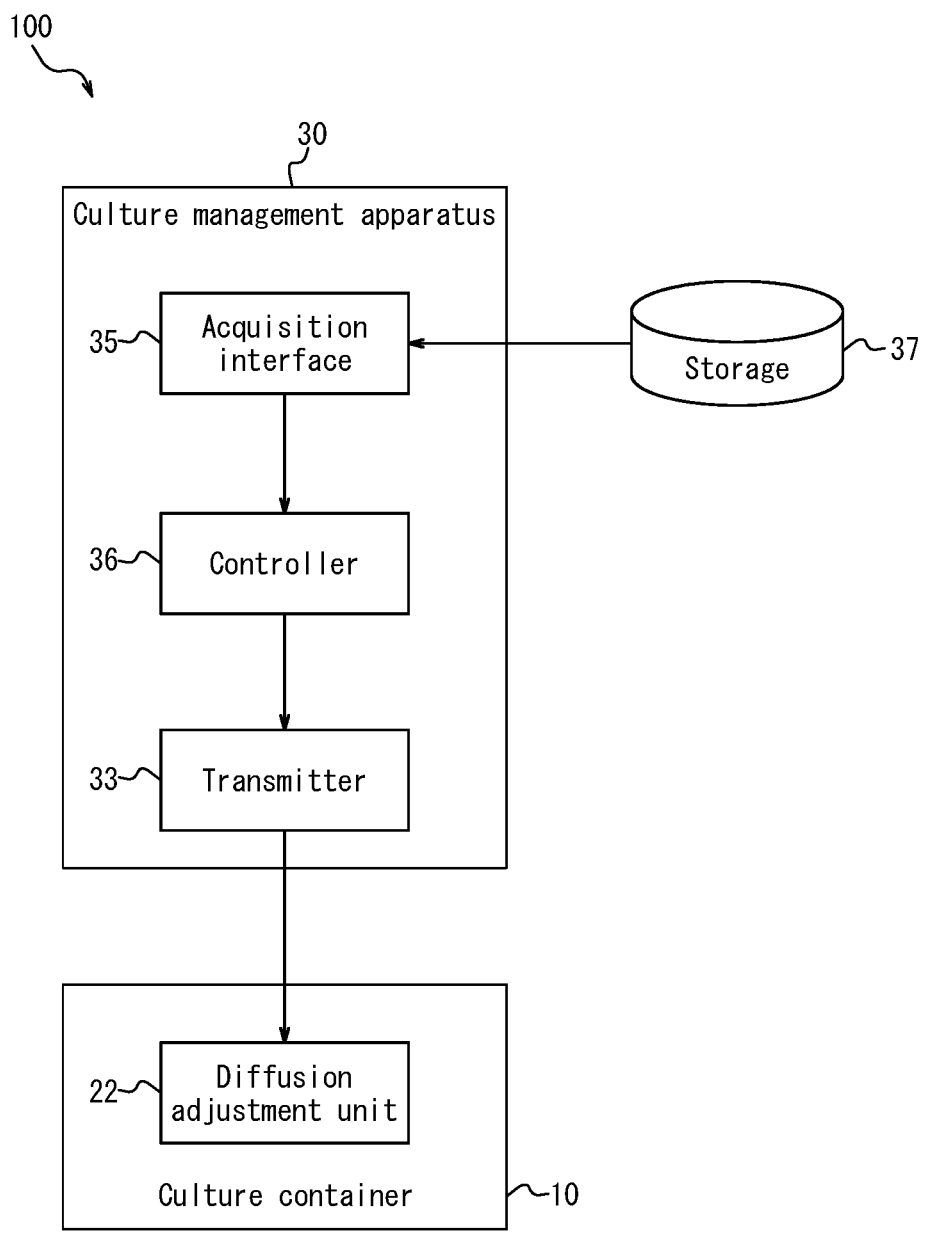
FIG. 10 is a functional block diagram illustrating an example of the basic structure of the culture system.

With reference to FIG. 10, the basic configuration of the culture system is described below. FIG. 10 is a functional block diagram illustrating an example of the basic structure of the culture system. As illustrated in FIG. 10, the culture management apparatus 30 includes an acquisition interface 35, a controller 36, and the transmitter 33.

Figure 17:
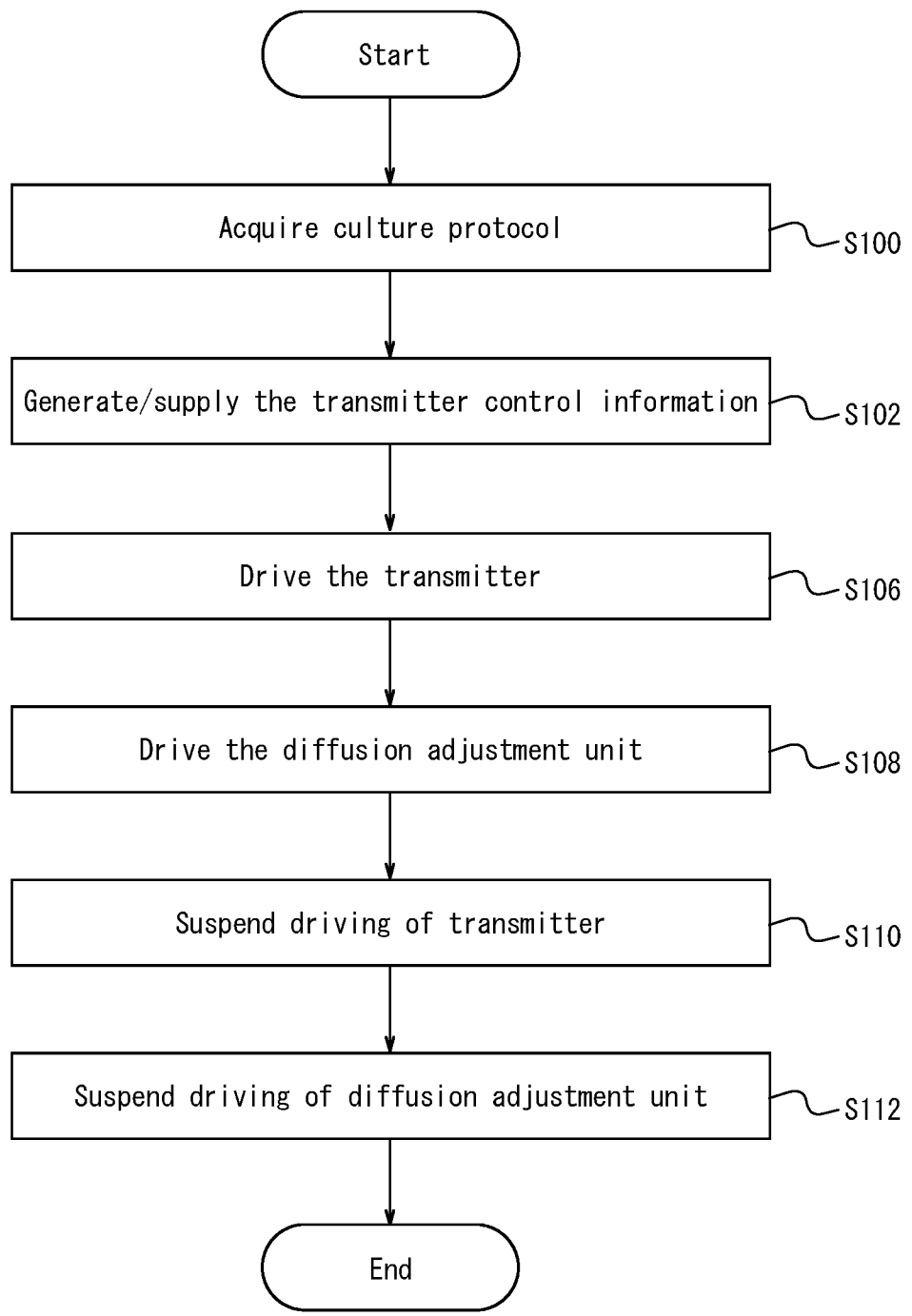
FIG. 17 is a flowchart illustrating an example of a method of adjusting the diffusion rate of an additive by a culture system.

An overview of operations of the culture system 100 is provided with reference to the schematic configuration of FIG. 10 and the flowchart of FIG. 17. The acquisition interface 35 acquires a culture protocol stored in a storage 37 and supplies the culture protocol to the controller 36 (step S100). The controller 36 refers to the culture protocol to generate transmitter control information for controlling transmission of the control signal 34 from the transmitter 33 and supplies the transmitter control information to the transmitter 33 (step S102). Based on the transmitter control information, the transmitter 33 transmits the control signal 34 for adjusting the diffusion rate of the additive to the diffusion adjustment unit 22 of the culture container 10 (step S106). The diffusion adjustment unit 22 is driven (structurally changes) by receipt of the control signal 34 and changes the diffusion rate of additive from the inside of the additive retention unit 20 to the outside of the additive retention unit 20 via the diffusion adjustment unit 22 (step S108). Based on the transmitter control information, the transmitter 33 suspends transmission of the control signal 34 (step S110). Upon suspension of the transmission of the control signal 34 from the transmitter 33, the diffusion adjustment unit 22 stops being driven (changes to the state before receipt of the control signal 34), and the diffusion rate of additive from the inside of the additive retention unit 20 to the outside of the additive retention unit 20 via the diffusion adjustment unit 22 returns to its original state (step S112). Adjustment of the diffusion rate of the additive from the inside of the additive retention unit 20 to the outside of the additive retention unit 20 in this way enables appropriate control of the amount of additive diffusing to the outside of the additive retention unit 20 and the timing of addition.

Next, the components of the above-described culture system 100 are described in detail.

The storage 37 may be a non-volatile memory or storage medium that can be written to and read from at any time, such as a solid state drive (SSD), a hard disk drive (HDD), an optical disc, or the like. The storage 37 may be provided inside the culture management apparatus 30. The storage 37 may be provided on a computer connected over a network.

The culture management apparatus 30 includes a central processing unit (CPU) and a program memory, which constitute a computer, and includes the above-described controller 36 and acquisition interface 35 as the parts that perform the control necessary for implementing the present embodiment. These parts are each implemented by the CPU executing programs stored in the program memory.

The transmitter 33 transmits an optical signal, an electric signal, an acoustic signal, a magnetic signal, or the like as the control signal 34. To increase the degree of freedom of control, a signal that can be operated wirelessly, in a non-contact manner, or remotely is preferably used as the control signal 34. In one example, the transmitter 33 transmits a control signal 34 of a specific type, intensity, and transmission time based on the transmitter control information. When an optical signal, such as near-infrared rays, is used as the control signal 34, the transmitter 33 in an example transmits a control signal 34 of a specific wavelength based on the transmitter control information.

The transmitter 33 may transmit the control signal 34 through the additive retention unit 20 to the diffusion adjustment unit 22, as illustrated in FIG. 9, or may transmit the control signal 34 to the diffusion adjustment unit 22 without the control signal 34 passing through the additive retention unit 20. To reduce the effect on the additive retained in the additive retention unit 20 insofar as possible, the transmitter 33 preferably transmits the control signal 34 to the diffusion adjustment unit 22 over a path that does not traverse the additive retention unit 20.

The culture management apparatus 30 may include a transport apparatus for moving the transmitter 33 inside the culture system 100. A configuration to move the transmitter 33 inside the culture system 100 enables movement of the transmitter 33 as necessary to a position appropriate for transmitting the control signal 34, thus enabling suitable transmission of the control signal 34 even when a plurality of the diffusion adjustment units 22 is provided, as described below.

Any of the above-described culture containers 10 may be used in the present culture system. For example, in an embodiment using a culture container 10 that includes a plurality of culture additive diffusion mechanisms 23 for one culture unit 11, as illustrated in FIG. 6, the controller 36 may refer to the culture protocol to generate transmitter control information for transmitting the control signal 34 to a predetermined diffusion adjustment unit 22 among the plurality of diffusion adjustment units 22. The transmitter 33 then transmits, to the predetermined diffusion adjustment unit 22, the control signal 34 for adjusting the diffusion rate of the additive based on the transmitter control information corresponding to the predetermined diffusion adjustment unit 22. The predetermined diffusion adjustment unit 22 adjusts the rate of diffusion of the additive to the culture unit 11 based on the control signal 34. This configuration enables independent control of addition of the additive from the plurality of culture additive diffusion mechanisms 23, thereby enabling addition of the additive to the culture unit 11 to be controlled more freely. For example, the additive retention units 20 of the plurality of diffusion adjustment units 22 can be caused to retain different types of additive to enable culturing while controlling the addition of a plurality of types of additive at independent times. Even when the additive retention units 20 of the plurality of diffusion adjustment units 22 are caused to retain the same type of additive, diffusion of the additive from the plurality of diffusion adjustment units 22 can be controlled for suitable adjustment of the concentration gradient of the additive in the culture unit 11. Control signals differing from each other in wavelength, irradiation duration, irradiation intensity, irradiation position (position of the transmitter 33 when transmitting the control signal 34), irradiation range, and the like can be used as the control signals for the diffusion adjustment units 22.

Figure 11:
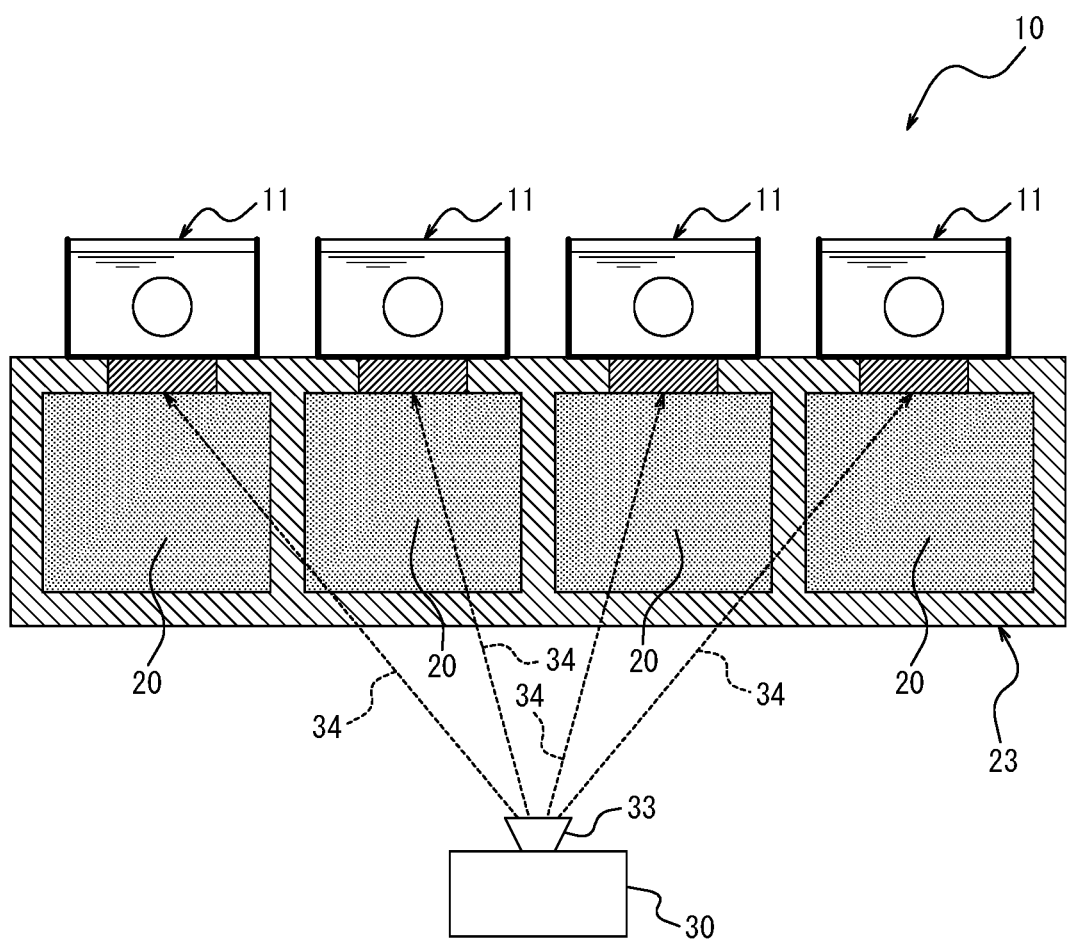
FIG. 11 illustrates the schematic configuration of an example of a culture system including a culture container signal transmission path that includes a plurality of culture units and additive diffusion mechanisms.

In an embodiment using a culture container 10 that includes a plurality of culture units 11 with a culture target and culture medium 13 introduced therein and a plurality of culture additive diffusion mechanisms 23 for the plurality of culture units 11, as illustrated in FIG. 11, the controller 36 may refer to the culture protocol to generate transmitter control information for transmitting the control signal 34 to the plurality of diffusion adjustment units 22 included in the plurality of culture additive diffusion mechanisms 23. The transmitter 33 then transmits, to the plurality of diffusion adjustment units, the control signal 34 for adjusting the diffusion rate of the additive based on the transmitter control information. The diffusion adjustment units adjust the rate of diffusion of the additive to the plurality of culture units 11 based on the control signal 34. FIG. 11 illustrates an example of the control signal 34 being transmitted from one transmitter 33 to the diffusion adjustment units 22, but a transport apparatus may be included for the transmitter 33 to transmit the control signal 34 to each diffusion adjustment unit 22 while moving. This culture system enables efficient and simple control of the addition of the additive to the culture medium 13 of the plurality of culture units 11 in parallel, thereby enabling efficient culturing of a large quantity of a culture target, such as cells.

In an embodiment using the culture container 10 illustrated in FIG. 11, the controller 36 may refer to the culture protocol to generate transmitter control information for transmitting the control signal 34 to a predetermined diffusion adjustment unit 22 among the plurality of diffusion adjustment units 22 included in the plurality of culture additive diffusion mechanisms 23. The transmitter 33 then transmits, to each predetermined diffusion adjustment unit 22, the control signal 34 for adjusting the diffusion rate of the additive based on the transmitter control information corresponding to the predetermined diffusion adjustment unit 22. The diffusion adjustment unit 22 adjusts the rate of diffusion of the additive from the predetermined diffusion adjustment unit 22 to the culture unit 11 based on the control signal 34. This configuration enables independent control of addition of the additive to the culture medium 13 of the plurality of culture units 11 for efficient culturing in parallel of culture targets under various culture conditions. Suitable culture conditions can therefore be studied and selected efficiently.

Figure 12:
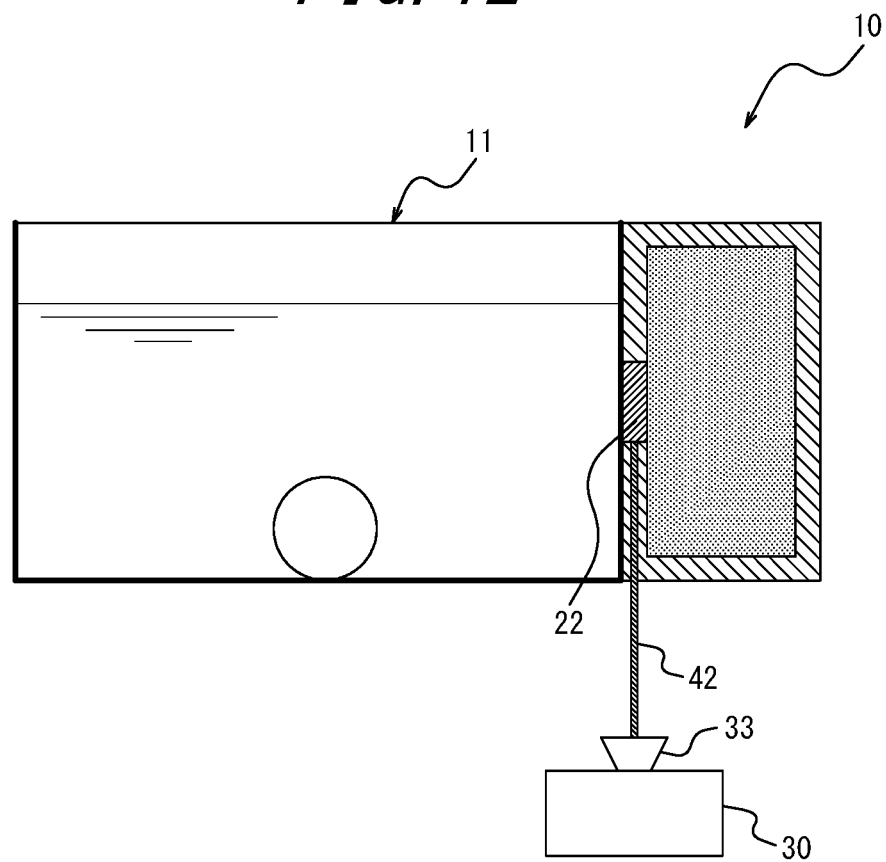
FIG. 12 illustrates the schematic configuration of an example of a culture system that includes a signal transmission path.

As illustrated in FIG. 12, a signal transmission path 42 for transmitting the control signal 34 to the diffusion adjustment unit 22 may be connected to the transmitter 33. When the signal transmission path 42 for transmitting the control signal 34 to the diffusion adjustment unit 22 is connected to the transmitter 33 in this way, the control signal 34 is not blocked or disrupted by external factors, thereby enabling the control signal 34 to be transmitted to the diffusion adjustment unit 22 more accurately.

One end of the signal transmission path 42 is connected to the transmitter 33 and the other end is connected to the diffusion adjustment unit 22 in the example in FIG. 12, but the other end need not be connected to the diffusion adjustment unit 22. In an example, the other end of the signal transmission path 42 connected to the transmitter 33 is installed to a point near the diffusion adjustment unit 22. Installing the other end of the signal transmission path 42 to a point near the diffusion adjustment unit 22 without connecting the signal transmission path 42 to the diffusion adjustment unit 22 can prevent blockage, disruption, or the like of the control signal 34 as compared to when the signal transmission path 42 is not included.

In an example, the other end of the signal transmission path 42 is not connected to the diffusion adjustment unit 22 but rather installed up to a point outside the culture container 10. Installing the other end of the signal transmission path 42 up to a point outside the culture container 10 without connection to the diffusion adjustment unit 22 enables the signal transmission path 42 to prevent blockage, disruption, or the like of the control signal 34 while being separated from the culture container 10. This facilitates replacement of the culture container 10. Hence, when the signal transmission path 42 is provided for a disposable culture container 10, the other end of the signal transmission path 42 is preferably installed up to the outside the culture container 10 without being connected to the diffusion adjustment unit 22. In an embodiment for transporting the culture container 10, as described below, transportation of the culture container 10 could be obstructed if the other end of the signal transmission path 42 is connected to the diffusion adjustment unit 22. Hence, when the signal transmission path 42 is provided in an embodiment for transporting the culture container 10, the other end of the signal transmission path 42 is preferably installed up to the outside the culture container 10 without being connected to the diffusion adjustment unit 22.

The type of signal transmission path 42 can be appropriately selected in accordance with the type of control signal 34. For example, when an electric signal is used as the control signal 34, a conducting wire can be used as the signal transmission path 42, whereas when the control signal 34 is an optical signal, an optical waveguide such as an optical fiber can be used.

The culture protocol defines at least an addition procedure of the additive. In an example, the culture protocol defines at least one piece of information (A) selected from among the group consisting of an addition amount of the additive, an addition duration (length of time of addition), a timing, and an addition concentration. The timing of addition refers to the timing at which addition of the additive starts and ends. The acquisition interface 35 acquires the information (A) and supplies the information (A) to the controller 36. The controller 36 refers to the information (A), generates transmitter control information that includes at least one piece of information (B) selected from among the group consisting of the intensity of the control signal 34 generated by the transmitter 33, the driving duration (the length of time of driving) of the transmitter 33, and the timing of driving, and supplies the transmitter control information to the transmitter 33. The transmitter 33 refers to the information (B) and transmits the control signal 34 to the diffusion adjustment unit 22 at a predetermined intensity, duration (length of time), and timing. The diffusion adjustment unit 22 receives the control signal 34 and supplies the additive to the culture medium 13 at a predetermined amount, duration (length of time), timing, and addition concentration. When the culture protocol thus defines at least one piece of information selected from among the group consisting of an addition amount of the additive, an addition duration, and a timing, the culture system can acquire the culture protocol and adjust at least one of the addition amount of the additive, the addition duration, and the timing.

When the culture container 10 includes a plurality of culture additive diffusion mechanisms 23, and the types of additives retained by the plurality of culture additive diffusion mechanisms 23 differ from each other, the culture protocol can define the type of additive to be added (information (C)). In this case, the acquisition interface 35 acquires the information on the type of additive to be added and supplies the information to the controller 36. The acquisition interface 35 further acquires information (information (D)) associating the position of the plurality of culture additive diffusion mechanisms 23 and the type of additive retained by each culture additive diffusion mechanism 23 and supplies the information (D) to the controller 36. In an example, the information (D) is defined in advance, in accordance with the type of culture container 10 in use, and is stored in the storage 37. The controller 36 refers to the information (C) and (D) to generate transmitter control information including information on the culture additive diffusion mechanism 23 to which the control signal 34 is to be transmitted. The controller 36 then supplies the transmitter control information to the transmitter 33. The transmitter 33 refers to the transmitter control information and transmits the control signal 34 to the diffusion adjustment unit 22 of the culture additive diffusion mechanism 23 that retains a predetermined type of additive. The predetermined diffusion adjustment unit 22 receives the control signal 34 and supplies the predetermined additive to the culture medium 13.

When the culture system acquires the degree of differentiation of the culture target (differentiation stage, growth stage, and the like of the culture target) using a culture target state measurement unit or the like as described below, the culture protocol may define the timing of the addition of the additive in accordance with the differentiation stage and the growth stage of the culture target. In other words, the culture protocol may define the start and end of addition during a specific differentiation stage and growth stage of the culture target. In an example, the culture container 10 includes a plurality of culture additive diffusion mechanisms 23, the types of additives retained by the plurality of culture additive diffusion mechanisms 23 differ from each other, and in accordance with the differentiation stage and growth stage of cells or the like, the culture protocol defines the preferred type of additive, addition amount, and addition duration in association with each differentiation stage and growth stage of the culture target.

Figure 13:
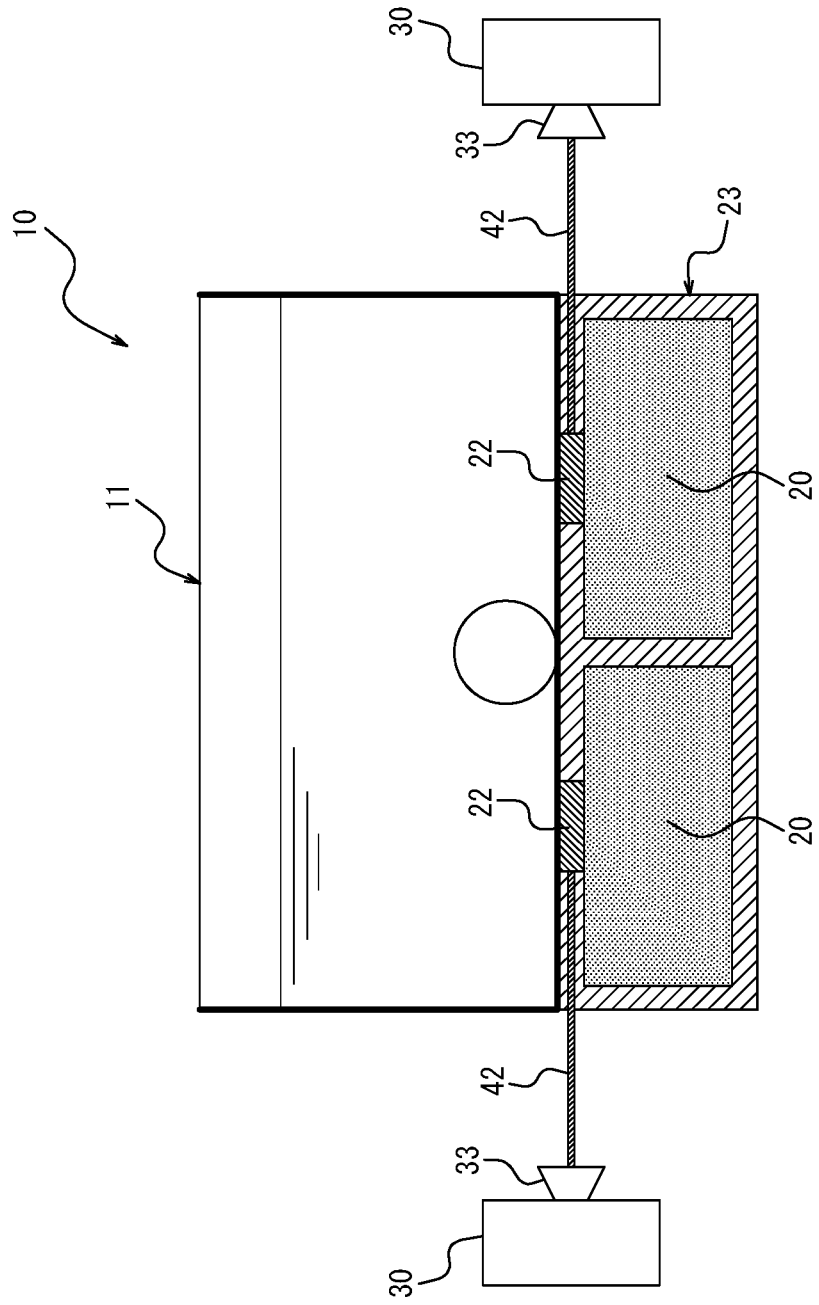
FIG. 13 illustrates the schematic configuration of an example of a culture system that uses a culture container that includes a plurality of culture units.

FIG. 13 schematically illustrates another embodiment of a culture system. As illustrated in FIG. 13, the culture container 10 may include a plurality of culture additive diffusion mechanisms 23, and a signal transmission path 42 for transmitting a control signal 34 to the diffusion adjustment unit 22 of each culture additive diffusion mechanism 23 may be connected to a transmitter 33. Transmission of the control signal 34 via the signal transmission path 42 in this way can prevent crosstalk between control signals 34 for a plurality of diffusion adjustment units 22. Accordingly, even when the diffusion adjustment units 22 are positioned near each other as illustrated in FIG. 13, the control signal 34 can be prevented from being transmitted to a nearby diffusion adjustment unit 22, thereby enabling the diffusion adjustment units 22 to be controlled independently. FIG. 13 illustrates an embodiment in which different transmitters 33 are connected to the signal transmission paths 42. Alternatively, a plurality of signal transmission paths 42 may be provided for one transmitter 33, and the signal transmission paths 42 for diffusion adjustment units 22 to which the control signal 34 is not to be transmitted may be cut off using a shutter, mask, or the like so that the transmitter 33 can transmit the control signal 34 to a specific diffusion adjustment unit 22.

Figure 14:
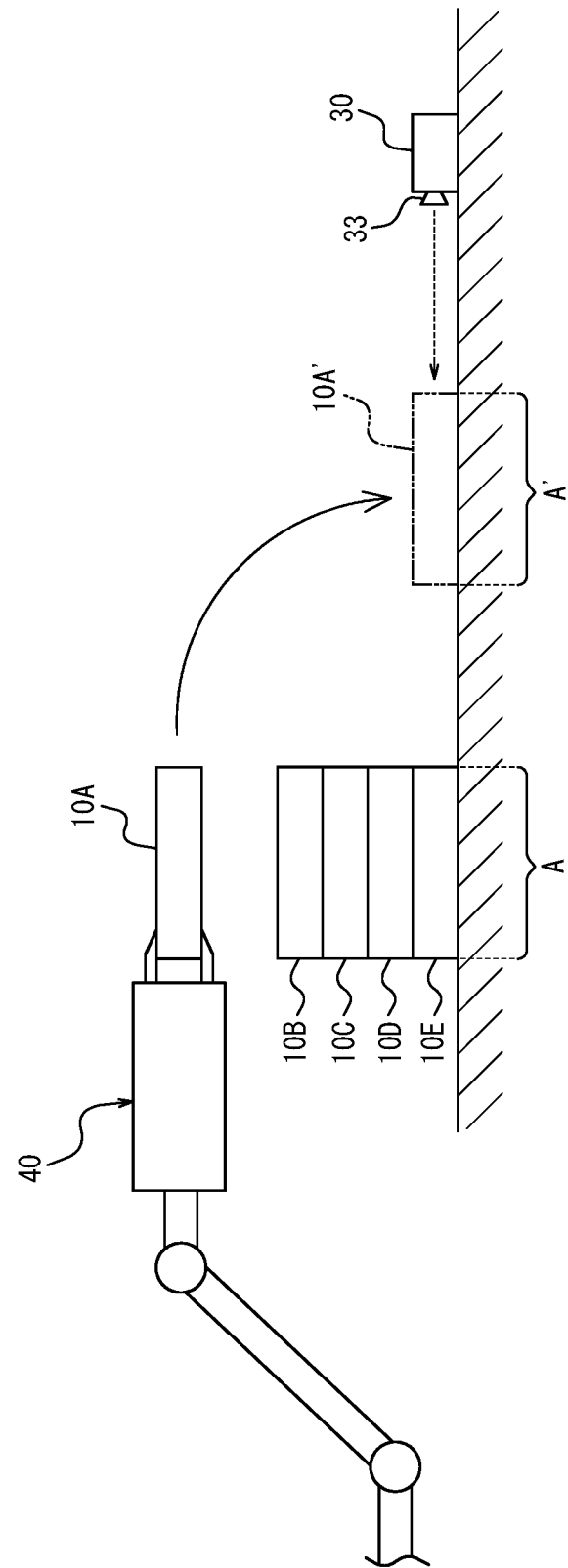
FIG. 14 illustrates the schematic configuration of an example of a culture system that uses a culture container that includes a plurality of additive diffusion mechanisms.

FIG. 14 schematically illustrates another embodiment of a culture system. As illustrated in FIG. 14, the culture system may include a plurality of culture containers 10 and further include a transport unit 40 configured to move at least one of the culture containers 10 from position A to a predetermined position. In the example in FIG. 14, the transport unit 40 transports one culture container 10A among the plurality of culture containers 10 to a predetermined position A. For the sake of illustration, the culture container 10A that is moved to position A' is referred to as culture container 10A'. The controller 36 creates transmitter control information a, b, c, d respectively for the plurality of culture containers 10A, 10B, 10C, 10D. The transmitter 33 transmits the control signal 34 to the diffusion adjustment unit 22 of the culture container 10A' based on the transmitter control information a corresponding to the culture container 10A' moved to the predetermined position. This configuration to move the culture container 10 to a predetermined position and transmit the control signal 34 to the culture container 10 moved to the predetermined position enables efficient mass production of cells automatically.

After the control signal 34 is transmitted, the culture container 10 is returned to the original position (A) by the transport unit 40.

The transport unit 40 may have any specific form, such as an automatic robot hand, as illustrated in FIG. 11, or a belt conveyor.

Figure 15:
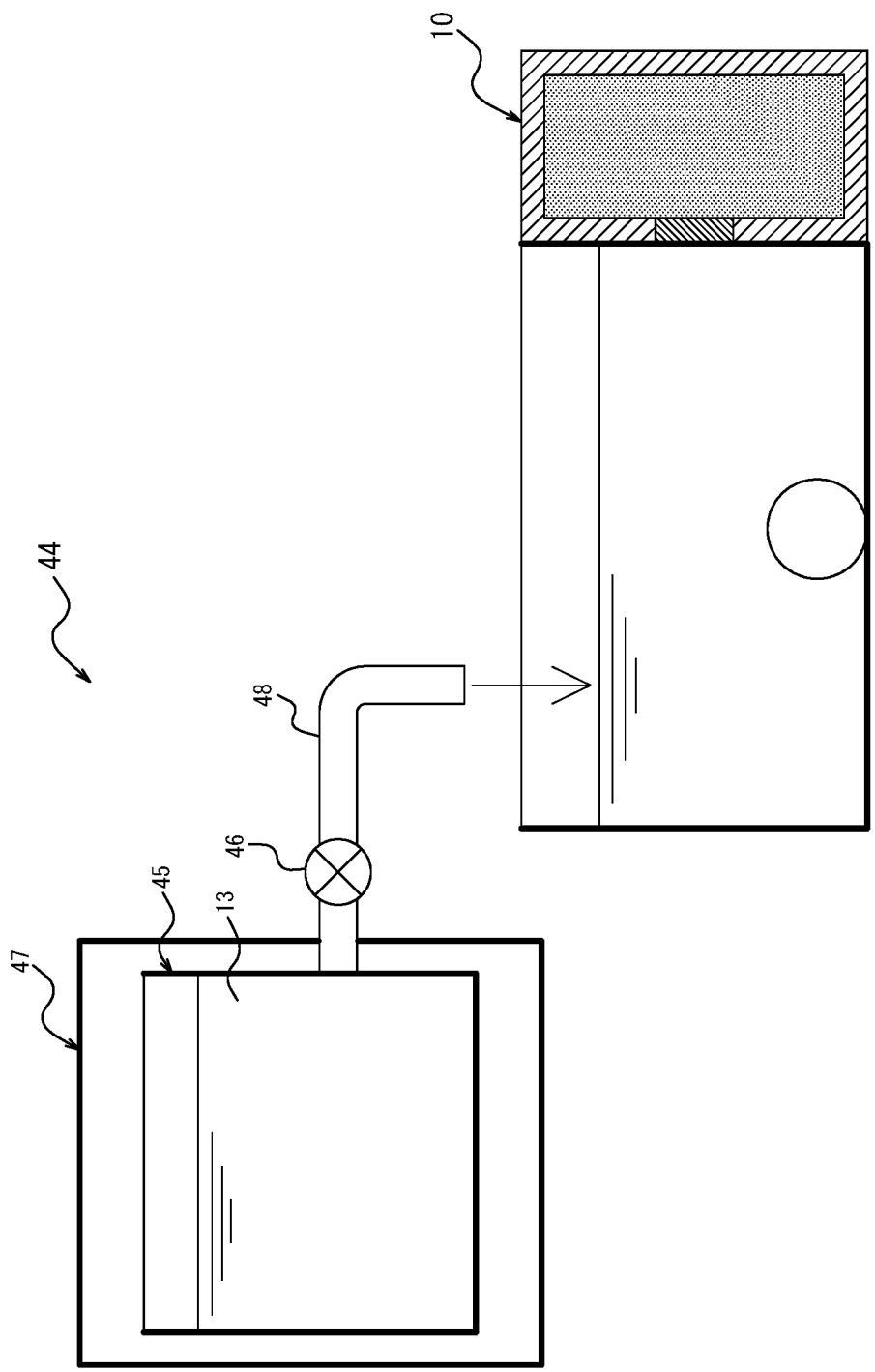
FIG. 15 illustrates the schematic configuration of an example of a culture system that includes a transport unit.

As illustrated in FIG. 15, the culture system may further include a culture medium supply unit 44 that introduces the culture medium 13 into the culture unit 11. The culture medium supply unit 44 includes a culture medium storage unit 45 for storing the culture medium 13, a culture medium preservation unit 47 for suitably storing the culture medium 13, a culture medium transfer route 48 for supplying the culture medium 13 to the culture unit 11, and a culture medium transfer unit 46 driven to supply the culture medium 13 via the culture medium transfer route 48. In the example in FIG. 12, the culture medium 13 is further supplied. When the culture medium supply unit 44 supplies the culture medium 13 to the culture unit 11 based on the culture medium supply unit control information in this way, the supply of the culture medium 13 can also be automated. This enables the culture target, such as cells, to be cultured more efficiently. In particular, it takes time and effort to supply the culture medium 13 manually when the culture container 10 includes a plurality of culture units 11 as illustrated in FIG. 5, or when a plurality of culture containers 10 is used. Automating the supply of the culture medium 13 as in the present embodiment enables the culture medium 13 to be introduced efficiently into the culture unit 11.

Embodiments of the culture medium storage unit 45 are not particularly limited, and containers or the like typically used to store the culture medium 13 can be used.

The culture medium preservation unit 47 may include a mechanism for cooling and freezing to prevent degradation of the culture medium component. The culture medium preservation unit 47 may store the culture medium 13 in a dry solid state and add an appropriate solvent to the culture medium 13 in the dry solid state when necessary.

As long as the culture medium transfer unit 46 can supply the necessary volume of culture medium 13 to the culture unit 11, the culture medium transfer unit 46 may, for example, be a dispenser, an inkjet, a pump, or the like.

The culture medium transfer route 48 can be a typical silicon tube, pipe, or the like.

While not illustrated, the culture system may further include a culture medium disposal unit to dispose unwanted culture medium 13 from the culture unit 11.

Figure 16:
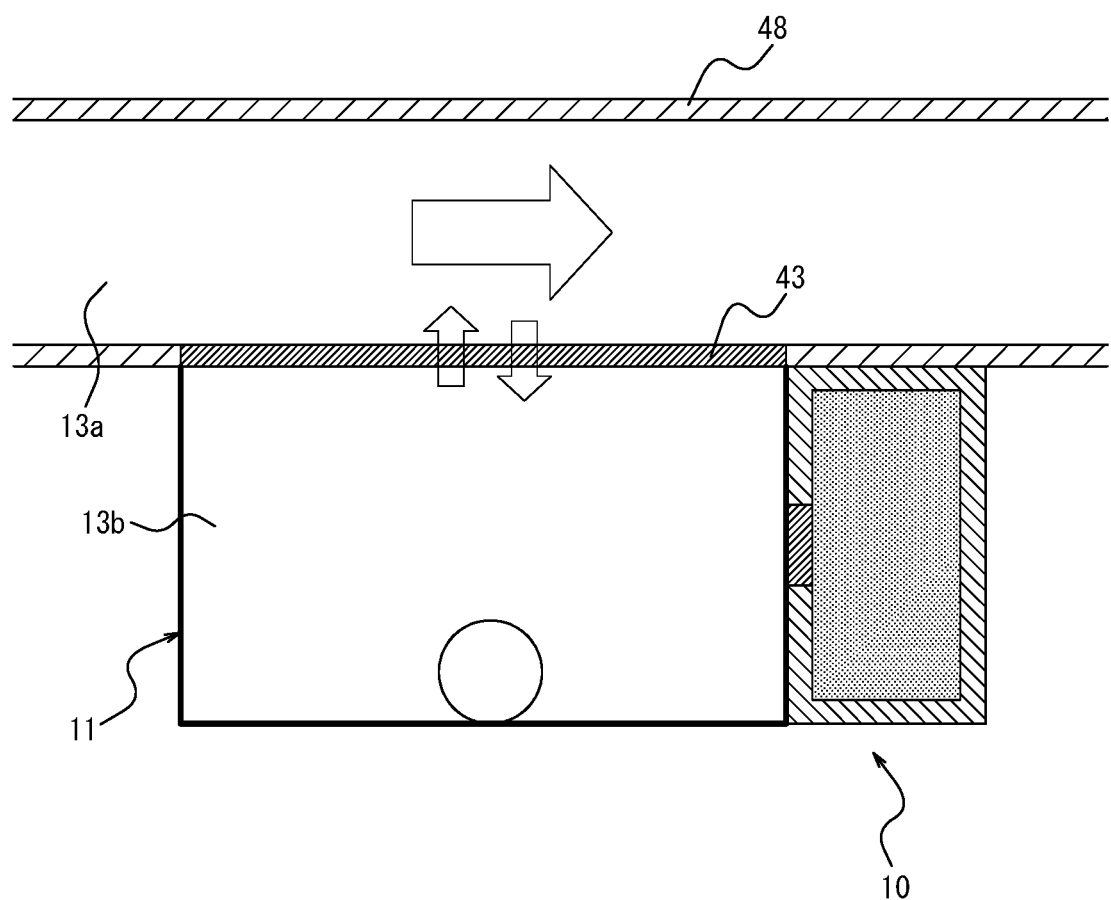
FIG. 16 illustrates the schematic configuration of an example of a culture system that includes a semi-permeable membrane unit formed by a semi-permeable membrane.

In an embodiment in which the culture system includes the culture medium supply unit 44, at least a portion of the culture container 10 may be a semi-permeable membrane unit 43 formed by a semi-permeable membrane, as illustrated in FIG. 16. The culture medium storage unit 45, the culture medium preservation unit 47, and the culture medium transfer unit 46 are not illustrated in FIG. 16. In the example in FIG. 16, the culture medium transfer route 48 is provided at the upper portion of the semi-permeable membrane unit 43, and culture medium 13a flows in the direction of the arrow through the culture medium transfer route 48. A fluid connection is formed via the semi-permeable membrane unit 43 between the culture medium 13b filling the culture unit 11 and the culture medium 13a flowing through the culture medium transfer route 48. When the culture target absorbs nutrients in the culture medium 13b and emits waste products as a result of culturing, the concentration of each component of the culture medium 13b in the culture unit 11 differs from that of the culture medium 13a flowing through the culture medium transfer route 48. This difference in concentration leads to an exchange of components, via the semi-permeable membrane unit 43, between the culture medium supplied from the culture medium supply unit 44 and the culture medium inside the culture container. Macromolecules that cannot pass through the semi-permeable membrane unit 43 are retained within the culture unit 11. Through component exchange, waste products in the culture medium 13b move to the culture medium 13a, and conversely, nutrients move from the culture medium 13a to the culture medium 13b.

The semi-permeable membrane forming the semi-permeable membrane unit 43 can be selected in accordance with the component to be exchanged in the fresh culture medium and the type of cells being cultured. The semi-permeable membrane can be a porous membrane such as regenerated cellulose (cellophane), acetyl cellulose, polyacrylonitrile, Teflon® (Teflon is a registered trademark in Japan, other countries, or both), a polyester-based polymer alloy, polysulfone, and the like.

The culture system may further include a culture target state measurement unit configured to measure the state of the culture target, such as cells, in the culture unit 11. The acquisition interface 35 acquires the measurement result of the state of the culture target using the culture target state measurement unit and supplies the measurement result to the controller 36. In addition to the above-described culture protocol, the controller 36 also refers to the measurement result of the state of the culture target to judge the state of the culture target, calculate an addition procedure of the additive in accordance with the state of the culture target, and generate transmitter control information. When the transmitter control information is generated with reference to the measurement result of the state of the culture target in this way, the additive can be added suitably in accordance with the state of the culture target.

In an example, the culture target is cells, and the culture target state measurement unit measures the degree of differentiation of the cells. The controller 36 refers to the measurement result of the degree of differentiation of the cells to generate transmitter control information such that the type and amount of additive corresponding to the degree of differentiation is added. The transmitter 33 refers to the transmitter control information and transmits a control signal 34 of a predetermined length to the diffusion adjustment unit 22 of the culture additive diffusion mechanism 23 in which a predetermined type of additive is retained. The diffusion adjustment unit 22 that receives the control signal 34 is driven for a predetermined time corresponding to the length of the control signal 34 and diffuses the additive. Adding the additive appropriately in accordance with the degree of differentiation of cells in this way enables the differentiation of cells to be controlled more suitably. This culture system 100 can, for example, also easily switch the type of additive in accordance with the degree of differentiation.

A measurement apparatus appropriate for the culture target is selected as the culture target state measurement unit. A measurement method that is not very invasive for the culture target, such as cells, and that does not adversely affect culturing and diffusion control of the additive is preferable for the culture target state measurement unit. The culture target state measurement unit may, for example, measure the state of the culture target by introducing a measurement reagent into the culture unit 11. The state of the culture target may also be measured by sampling the culture medium 13 from the culture unit 11 and analyzing the sample with an analysis device. Various other measurement methods can be used to measure the state of the culture target in the culture target state measurement unit, such as cell imaging, fluorometry, Raman spectroscopy, infrared spectroscopy, ultrasonography, or the like. These measurement methods may be used alone, or a plurality thereof may be used in combination.

The specific configuration of the classification and learning process for the controller 36 to judge the state of the culture target is not restricted.

The following machine learning methods, for example, may be used alone or in combination.

Support vector machine (SVM)
Clustering
Inductive logic programming (ILP)
Genetic programming (GP)
Bayesian network (BN)
Neural network (NN)

In the case of using a neural network, the data used is preferably processed in advance for input to the neural network. Such processing may use a method such as data argumentation in addition to organizing the data in a one-dimensional array or a multi-dimensional array.

In the case of using a neural network, a convolutional neural network (CNN) that includes convolution processing may be used. In greater detail, a convolution layer that perform convolution calculation may be provided as one or more layers included in a neural network, and a filter operation (product-sum operation) may be performed on the input data to be inputted to the layer. When the filter operation is performed, processing such as padding may also be performed, or an appropriately set stride width may be adopted.

A multilayer or ultra-multilayer neural network with several tens to several thousands of layers may be used as the neural network.

The machine learning used for judgment processing of the state of the culture target by the controller 36 may be supervised learning or unsupervised learning.

In this way, the controller 36 in an example includes a machine learning mechanism and can refer to the learning result of the machine learning mechanism to judge the state of the culture target. This configuration enables the controller 36 to execute processing to judge the state of the culture target accurately.

The culture system may further include an additive measurement unit configured to measure the concentration of the additive included in the culture medium 13 in the culture unit 11. Other than the average concentration of the additive in the culture unit 11, the additive measurement unit can also measure the local concentration of the additive in the culture unit 11, the concentration distribution in the culture unit 11, and the like as the concentration of the additive. The acquisition interface 35 acquires the measurement result of the concentration of the additive using the additive measurement unit and supplies the measurement result to the controller 36. The controller 36 refers to the measurement result of the concentration of the additive in addition to the above-described culture protocol and generates the transmitter control information. When the transmitter control information is generated with reference to the measurement result of the concentration of the additive in this way, the additive can be added while the concentration of the additive is monitored. This enables a suitable amount of the additive to be added reliably, which increases production stability of the culture target 12.

The type of additive measurement unit may be selected appropriately in accordance with the type of additive. For example, the additive measurement unit may include a sampling apparatus and a measuring device for high-speed liquid chromatography, mass spectrometry, or the like, and culture medium 13 in the culture unit 11 sampled by the sampling apparatus may be measured by the measuring device. The additive measurement unit may measure the concentration of the additive using a method that does not require sampling, such as spectroscopic analysis. Measurement of the additive may be facilitated by use of an additive labeled with fluorescent molecules. A material with a diffusion coefficient similar to that of the additive targeted for measurement may be diffused at the same time as the additive, and the concentration of the additive may be estimated or the like by measuring the similar material.

The culture system may include a culture environment maintenance unit for maintaining a physical parameter inside the culture unit 11 within a certain range. The culture environment can be maintained suitably by maintaining the physical parameter inside the culture unit 11 within a certain range. Cells that are sensitive to changes in physical parameters can therefore be cultured efficiently. In general, the properties of cells after culturing are thought to differ due to differences in the culture environment. When the culture system includes the culture environment maintenance unit, however, cells can be cultured while conditions suitable for culturing are maintained.

Examples of the physical parameters maintained within a certain range by the culture environment maintenance unit include temperature, humidity, partial pressure of gasses such as oxygen and carbon dioxide, and atmospheric pressure. The culture environment maintenance unit can be selected appropriately in accordance with the targeted physical parameter. Examples include a thermostat and a multi-gas incubator.

An example of a method of producing cells according to the present disclosure is described next. The method of producing cells uses the above-described culture system. In greater detail, the method of producing cells is used in a culture system including the culture container 10 according to the present disclosure and the culture management apparatus 30. The culture management apparatus 30 includes the acquisition interface 35, the controller 36, and the transmitter 33. The method includes acquiring, using the acquisition interface 35, the culture protocol that defines at least an addition procedure of the additive; referring, using the controller 36, to the culture protocol to generate transmitter control information; transmitting, using the transmitter 33, the control signal 34 for adjusting the diffusion rate of the additive to the diffusion adjustment unit 22 based on the transmitter control information; and adjusting, using the diffusion adjustment unit 22, the diffusion rate of the additive based on the control signal 34. Such a method of producing cells enables cell production while efficiently and easily adjusting the addition of additive to the culture medium 13.

The culture system according to the present disclosure can be used not only to produce cells but also to produce tissue that includes a plurality of cells.

EXAMPLES

Next, a cell culture carrier and a cell culture container according to the present disclosure are described in greater detail with Examples.

Example 1

The materials used in Example 1 are as follows.
—Porous Material

As the porous material, 4% agarose gel particles (CarboxyLink; Thermo Fisher Scientific) with a carboxyl group on the surface were used.
—Stimulus-Responsive Polymer Material Poly(allylamine-co-allylurea) gel was used as the stimulus-responsive polymer material. This gel was produced by referring to pages 182-184 of The Protocols for the Preparation of DDS Carriers (published by CMC) and introducing an ureido group on primary amine of 93% allylamine with respect to poly(allylamine) (Nittobo Medical) having a molecular weight of 15,000. Since an amino group is also included in the ureido group, a gel was formed by using glutaraldehyde to cross-link the amino groups inside and between only a portion of the molecules.

Plentiful amino groups were included in this gel. Consequently, the other component of these hydrogen bonds switched, in accordance with temperature, between the amino group in a poly(allylamine-co-allylurea) molecule and a water molecule in the solvent, making it possible to cause a phase transition between aggregation and swelling.

The phase transition temperature of this gel was 44° C. under physiological conditions of an NaCl concentration of 150 mM and pH 7.5. Swelling occurred at a temperature equal to or greater than the phase transition temperature, the permeability of the material increased, and solubility in water increased.
—Control Signal Receiving Material Gold nanorods (Sigma-Aldrich) having an absorption peak at a wavelength of 808 nm, modified by amino groups on the surface, and having a diameter of 10 nm were used as the control signal receiving material.
—Control Signal A high-output fiber output LD light source 808 nm (As One) was used as a control signal source.
—Cell Housing A TC-treated 96 well plate (Corning) was used as the cell housing.
—Additive and Cultured Cells VEGF-A, which is a vascular endothelial growth factor, was used as the additive.

Human umbilical vein endothelial cells (HUVECs) were used as the cultured cells. HUVECs are used in physiology, such as blood coagulation and angiogenesis, and pharmacological testing. EBM™ endothelial cell growth basal medium (LONZA), without the addition of VEGF, was used as the culture medium.
—Production of Cell Culture Carrier The carboxyl group on the agarose gel particle surface of the porous material was activated using EDC and sulfo-NHS. The activation reaction was performed at room temperature in a MES buffer at pH 6.0. A material including an amino group with a covalent bond was thereby fixed on the agarose gel particles.

The resulting agarose gel particles were washed with the MES buffer, and amino group-modified gold nanorods were then reacted in phosphate buffered saline at pH 7.2.

Next, the synthesized poly(allylamine-co-allylurea) gel was reacted, and gold nanorods and poly(allylamine-co-allylurea) gel were fixed to the surface of the agarose gel particles via a portion of the amino groups in the gel. Unreacted gold nanorods and gel were removed by washing. A Complex 1 of a cell culture stimulus-responsive substrate and a porous material was thus formed.

The resulting Complex 1 was immersed in a pH 7.5, 10 mM HEPES buffer with 10 mM of NaCl added thereto. Under these conditions, the phase transition temperature lowers, and the stimulus-responsive polymer material swells at room temperature, enabling the additive to be incorporated.

The supernatant was removed so that the particles remained, and a HEPES buffer having an additive of VEGF dissolved therein was added. The VEGF penetrated the stimulus-responsive polymer material in the swollen state by diffusion and was incorporated in the porous material. A cell culture carrier 1 was thereby produced.

Next, the cell culture carrier 1 was transferred to the culture medium. The NaCl concentration thereby increased, and the phase transition temperature became 40° C. or greater, enabling VEGF to be retained in the porous material. The particles with VEGF incorporated therein were stored at 4° C. until use.
—Cell Culture The HUVECs suspended in the culture medium were disseminated on a culture plate, and the cells were adhered by culturing in an incubator at 5% $CO_2$ and 37° C.

After replacement with fresh culture medium, the cell culture carrier 1 was introduced. The stimulus-responsive polymer material was locally heated by irradiation with near-infrared light and swelled, increasing the solubility in water.

The enclosed VEGF consequently diffused and was released into the culture medium, which accelerated growth of the HUVECs. After the VEGF diffusion amount reached the necessary amount, irradiation of near-infrared light was suspended to prevent the VEGF from affecting the experimental results by acting on cell metabolism. The release of VEGF was thereby suspended.

REFERENCE LITERATURE

1) Ultrasound-Induced Gelation of Organic Fluids with Metallated Peptides, K. Isozaki, H. Takaya, and T. Naota, Angew. Chem. Int. Ed., 46, 2855-2857 (2007).
2) Tunable, temperature-responsive polynorbornenes with side chains based on an elastin peptide sequence. R. M. Conrad, R. H. Grubbs, Angew. Chem., Int. Ed., 48, 8328 (2009).

INDUSTRIAL APPLICABILITY

The culture additive diffusion mechanism, culture container, culture system, and method of producing cells according to the present disclosure can be used in the fields of regenerative medicine, drug discovery, and cellular agriculture.

The invention claimed is:

1. A culture system comprising:
a culture container and a culture management apparatus;
wherein the culture container comprises a culture additive diffusion mechanism and a culture unit into which a culture target and a culture medium are introduced;
the culture additive diffusion mechanism comprises:
an additive retention unit configured to retain an additive used in a culture; and
a diffusion adjustment unit configured to adjust a diffusion rate of the additive from an inside of the additive retention unit to an outside of the additive retention unit,
wherein the culture unit and the culture additive diffusion mechanism are connected via the diffusion adjustment unit;
wherein the culture management apparatus comprises an acquisition interface, a controller, and a transmitter;
wherein the acquisition interface is configured to acquire a culture protocol that defines at least an addition procedure of the additive;
wherein the controller is configured to refer to the culture protocol to generate transmitter control information;
wherein the transmitter is configured to transmit a control signal for adjusting the diffusion rate of the additive to the diffusion adjustment unit based on the transmitter control information;
wherein the diffusion adjustment unit is configured to adjust the diffusion rate of the additive based on the control signal;
wherein the diffusion adjustment unit consists of a temperature-responsive material and a near-infrared absorber;
wherein an entire periphery of the additive retention unit is surrounded by the diffusion adjustment unit, or an impermeable unit and the diffusion adjustment unit;
wherein the culture system further comprises:
a plurality of the culture containers; and
a transport unit configured to move at least one culture container among the plurality of culture containers to a predetermined position;
wherein the controller is configured to refer to the culture protocol to generate, for each culture container among the plurality of culture containers, transmitter control information for adding the additive to the culture container; and wherein based on the transmitter control information corresponding to the culture container located at the position, the transmitter is configured to transmit the control signal to the diffusion adjustment unit of the culture container moved to the position.

2. The culture system of claim 1, wherein the diffusion adjustment unit is configured to change the diffusion rate of the additive in accordance with a change in at least one environmental parameter.

3. The culture system of claim 1, wherein the diffusion adjustment unit comprises a stimulus-responsive material and is configured to change the diffusion rate of the additive in accordance with at least one stimulus.

4. The culture system of claim 1,
wherein the diffusion adjustment unit further comprises a near-infrared absorber that absorbs near-infrared rays, and the stimulus-responsive material is a temperature-responsive material; and
wherein the temperature-responsive material changes the diffusion rate of the additive in accordance with a temperature change of the near-infrared absorber.

5. The culture system of claim 1, wherein the culture container comprises a plurality of the culture units.

6. The culture system of claim 1, wherein the culture container comprises a plurality of the culture additive diffusion mechanisms.

7. The culture system of claim 6, wherein the culture additive diffusion mechanisms retain different types of the additive from each other.

8. The culture system of claim 1, further comprising:
a culture medium supply unit configured to supply culture medium to the culture unit;
wherein the culture medium supply unit comprises a culture medium storage unit, a culture medium preservation unit, a culture medium transfer unit, and a culture medium transfer route;
wherein the culture protocol defines a supply procedure of the culture medium;
wherein the controller is configured to refer to the culture protocol to generate culture medium supply unit control information; and
wherein the culture medium supply unit is configured to supply the culture medium to the culture unit based on the culture medium supply unit control information.

9. The culture system of claim 1, further comprising:
a culture medium supply unit configured to supply culture medium to the culture unit;
wherein the culture medium supply unit comprises a culture medium storage unit, a culture medium preservation unit, a culture medium transfer unit, and a culture medium transfer route;
wherein at least a portion of the culture container is a semi-permeable membrane unit formed by a semi-permeable membrane;
wherein a fluid connection is formed between the culture container and the culture medium transfer route via the semi-permeable membrane unit; and
wherein a component of the culture medium supplied from the culture medium supply unit via the semi-permeable membrane unit and the culture medium inside the culture container are exchanged.

10. The culture system of claim 1, further comprising:
a culture target state measurement unit configured to measure a state of the culture target in the culture unit;
wherein the controller is configured to refer additionally to a measurement result of the culture target by the culture target state measurement unit to generate the transmitter control information.

11. The culture system of claim 1, further comprising:
an additive measurement unit configured to measure a concentration of the additive included in the culture medium in the culture unit;
wherein the controller is configured to refer additionally to a measurement result of the concentration of the additive by the additive measurement unit to generate the transmitter control information.

12. A method of producing cells, the method using the culture system of claim 1.

* * * * *